(12) United States Patent
Skog et al.

(10) Patent No.: US 10,988,755 B2
(45) Date of Patent: Apr. 27, 2021

(54) METHOD FOR ISOLATION OF NUCLEIC ACID CONTAINING PARTICLES AND EXTRACTION OF NUCLEIC ACIDS THEREFROM

(71) Applicant: Exosome Diagnostics, Inc., Cambridge, MA (US)

(72) Inventors: Johan Karl Olov Skog, Charlestown, MA (US); Leileata M. Russo, New York, NY (US)

(73) Assignee: Exosome Diagnostics, Inc., Waltham, MA (US)

( * ) Notice: Subject to any disclaimer, the term of this patent is extended or adjusted under 35 U.S.C. 154(b) by 580 days.

(21) Appl. No.: 14/877,531

(22) Filed: Oct. 7, 2015

(65) Prior Publication Data

US 2016/0024491 A1    Jan. 28, 2016

Related U.S. Application Data

(63) Continuation of application No. 13/883,673, filed as application No. PCT/US2011/060251 on Nov. 10, 2011, now abandoned.

(60) Provisional application No. 61/412,369, filed on Nov. 10, 2010.

(51) Int. Cl.
  *C12N 15/10* (2006.01)

(52) U.S. Cl.
  CPC .................................. *C12N 15/1003* (2013.01)

(58) Field of Classification Search
  CPC .................................................. C12N 15/1003
  See application file for complete search history.

(56) References Cited

U.S. PATENT DOCUMENTS

| | | | |
|---|---|---|---|
| 5,219,727 A | 6/1993 | Wang et al. |
| 5,538,871 A | 7/1996 | Nuovo et al. |
| 5,547,859 A | 8/1996 | Goodman |
| 5,556,773 A | 9/1996 | Yourno |
| 5,582,981 A | 12/1996 | Toole et al. |
| 5,639,606 A | 6/1997 | Willey |
| 5,639,611 A | 6/1997 | Wallace et al. |
| 5,811,250 A | 9/1998 | Solum |
| 5,840,867 A | 11/1998 | Toole et al. |
| 6,004,755 A | 12/1999 | Wang |
| 6,329,179 B1 | 12/2001 | Kopreski |
| 6,525,154 B1 | 2/2003 | Shea et al. |
| 6,607,898 B1 | 8/2003 | Kopreski et al. |
| 6,759,217 B2 | 7/2004 | Kopreski |
| 6,794,135 B1 | 9/2004 | Kopreski et al. |
| 6,812,023 B1 | 11/2004 | Lamparski et al. |
| 6,893,837 B2 | 5/2005 | Slamon et al. |
| 6,899,863 B1 | 5/2005 | Dhellin et al. |
| 6,913,879 B1 | 7/2005 | Schena |
| 6,916,634 B2 | 7/2005 | Kopreski |
| 6,939,671 B2 | 9/2005 | Kopreski |
| 6,994,960 B1 | 2/2006 | Foote et al. |
| 7,074,563 B2 | 7/2006 | Köster |
| 7,186,512 B2 | 3/2007 | Martienssen et al. |
| 7,198,893 B1 | 4/2007 | Köster et al. |
| 7,198,923 B1 | 4/2007 | Abrignani et al. |
| 7,332,533 B2 | 2/2008 | Kim |
| 7,332,552 B2 | 2/2008 | Benicewicz |
| 7,332,553 B2 | 2/2008 | Sellergren et al. |
| 7,364,848 B2 | 4/2008 | Van Beuningen et al. |
| 7,378,245 B2 | 5/2008 | Liu |
| 7,384,589 B2 | 6/2008 | Hart et al. |
| 7,671,010 B2 | 3/2010 | Arap et al. |
| 7,691,383 B2 | 4/2010 | Chakrabarty et al. |
| 7,776,523 B2 | 8/2010 | Garcia |
| 7,807,183 B2 | 10/2010 | Hong et al. |
| 2002/0106684 A1 | 2/2002 | Kopreski |
| 2003/0077808 A1 | 4/2003 | Rosen |
| 2005/0003426 A1 | 1/2005 | Ranum et al. |
| 2005/0250100 A1 | 11/2005 | Hayashizaki |
| 2006/0081516 A1 | 4/2006 | Hendrickson |
| 2006/0116321 A1 | 6/2006 | Robbins et al. |
| 2006/0160087 A1 | 7/2006 | McGrath et al. |
| 2006/0223072 A1 | 10/2006 | Boyes et al. |

(Continued)

FOREIGN PATENT DOCUMENTS

| | | |
|---|---|---|
| CA | 2453198 A1 | 7/2005 |
| CA | 2676113 A1 | 1/2009 |

(Continued)

OTHER PUBLICATIONS

Alvarez ML, Khosroheidari M, Kanchi Ravi R, DiStefano JK. Comparison of protein, microRNA, and mRNA yields using different methods of urinary exosome isolation for the discovery of kidney disease biomarkers. Kidney Int. Nov. 2012; 82(9):1024-32. Epub Jul. 11, 2012. (Year: 2012).*

Hunter MP, Ismail N, Zhang X, Aguda BD, Lee EJ, Yu L, Xiao T, Schafer J, Lee ML, Schmittgen TD, Nana-Sinkam SP, Jarjoura D, Marsh CB. Detection of microRNA expression in human peripheral blood microvesicles. PLoS One. 2008; 3(11):e3694. Epub Nov. 11, 2008. (Year: 2008).*

Jacquillet G, Hoorn EJ, Vilasi A, Unwin RJ. Urinary vesicles: in splendid isolation. Nephrol Dial Transplant. Jun. 2013; 28(6):1332-5. Epub Jan. 24, 2013. (Year: 2013).*

Miranda KC, Bond DT, McKee M, Skog J, Păunescu TG, Da Silva N, Brown D, Russo LM. Nucleic acids within urinary exosomes/microvesicles are potential biomarkers for renal disease. Kidney Int. Jul. 2010; 78(2):191-9. Epub Apr. 28, 2010. (Year: 2010).*

(Continued)

*Primary Examiner* — Teresa E Strzelecka
*Assistant Examiner* — Olayinka A Oyeyemi
(74) *Attorney, Agent, or Firm* — Cooley LLP; Ivor R. Elrifi; Matthew Pavao

(57) ABSTRACT

A method for extracting nucleic acids from a biological sample by isolating nucleic acid-containing particles from the biological sample by one or more centrifugation procedures, performing one or more steps to mitigate adverse factors that prevent or might prevent high quality nucleic acid extraction, and extracting nucleic acids from the isolated particles. The centrifugation procedures are performed at a speed not exceeding about 200,000 g. The extracted nucleic acids contain both 18S and 28S rRNA.

9 Claims, 4 Drawing Sheets

(56) References Cited

U.S. PATENT DOCUMENTS

| | | |
|---|---|---|
| 2007/0104738 A1 | 5/2007 | Tatischeff et al. |
| 2007/0105105 A1 | 5/2007 | Clelland |
| 2007/0254351 A1 | 11/2007 | Abrignani et al. |
| 2007/0298118 A1 | 12/2007 | Lotvall et al. |
| 2008/0003575 A1 | 1/2008 | Michalik et al. |
| 2008/0268429 A1 | 10/2008 | Pietrzkowski et al. |
| 2008/0287669 A1 | 11/2008 | Braman et al. |
| 2009/0169636 A1 | 7/2009 | O'Hagan et al. |
| 2009/0220944 A1 | 9/2009 | Fais et al. |
| 2009/0227533 A1 | 9/2009 | Bader |
| 2010/0008978 A1 | 1/2010 | Drummond et al. |
| 2010/0075315 A1 | 3/2010 | Pietrzkowski |
| 2010/0184046 A1 | 7/2010 | Klass |
| 2010/0196426 A1* | 8/2010 | Skog .................... C12Q 1/6806 424/400 |
| 2010/0209355 A1 | 8/2010 | Chakrabarty et al. |
| 2010/0255514 A1 | 10/2010 | Rak |
| 2011/0003704 A1 | 1/2011 | Skog et al. |
| 2011/0053157 A1 | 3/2011 | Skog et al. |
| 2011/0081651 A1 | 4/2011 | Hillan |
| 2011/0195426 A1* | 8/2011 | Russo ................ C12N 15/1017 435/6.17 |
| 2012/0115160 A1* | 5/2012 | D'Souza-Schorey ........................ G01N 33/5076 435/7.1 |
| 2012/0142001 A1 | 6/2012 | Skog et al. |
| 2012/0238467 A1 | 9/2012 | Taylor |
| 2013/0040833 A1 | 2/2013 | Noerholm et al. |
| 2013/0131194 A1 | 5/2013 | Skog et al. |
| 2013/0295574 A1 | 11/2013 | Skog et al. |
| 2014/0194319 A1 | 7/2014 | Skog et al. |
| 2014/0194613 A1 | 7/2014 | Skog et al. |
| 2016/0348095 A1 | 12/2016 | Russo et al. |
| 2016/0362678 A1 | 12/2016 | Skog et al. |
| 2017/0114389 A1 | 4/2017 | Russo et al. |
| 2017/0314075 A1 | 5/2017 | Skog et al. |
| 2018/0051335 A9 | 2/2018 | Skog et al. |

FOREIGN PATENT DOCUMENTS

| | | | |
|---|---|---|---|
| CA | 2699646 A1 | 3/2009 | |
| CN | 101085349 A | 12/2007 | |
| EP | 2202522 A1 | 6/2010 | |
| JP | H08-509806 A | 10/1996 | |
| JP | 2002521071 A | 7/2002 | |
| JP | 2002535665 A | 10/2002 | |
| JP | 2003514523 A | 4/2003 | |
| JP | 2003531864 A | 10/2003 | |
| JP | 2008501336 A | 1/2008 | |
| JP | 2008035779 A | 2/2008 | |
| JP | 2008509806 A | 4/2008 | |
| JP | 2008541699 A | 11/2008 | |
| JP | 2010534480 A | 11/2010 | |
| JP | 2011-510663 A | 4/2011 | |
| JP | 5156829 B2 | 3/2013 | |
| WO | WO 1994/011018 A1 | 5/1994 | |
| WO | WO 1994/022018 A1 | 9/1994 | |
| WO | WO 2000/004194 A1 | 1/2000 | |
| WO | WO 2000/006780 A1 | 2/2000 | |
| WO | WO 2001/036601 A1 | 5/2001 | |
| WO | WO-0136601 A1 * | 5/2001 | ........... C07K 14/005 |
| WO | WO 2001/082958 A2 | 11/2001 | |
| WO | WO 2002/099064 A2 | 12/2002 | |
| WO | WO 2003/023065 A1 | 3/2003 | |
| WO | WO 2003/050290 A2 | 6/2003 | |
| WO | WO 2003/076603 A2 | 9/2003 | |
| WO | WO 2005/000098 A3 | 1/2005 | |
| WO | WO 2005/081867 A3 | 9/2005 | |
| WO | WO 2005/121359 A1 | 12/2005 | |
| WO | WO 2005/121369 A2 | 12/2005 | |
| WO | WO-2005121369 A2 * | 12/2005 | ......... A61K 47/6901 |
| WO | WO 2006/020707 A2 | 2/2006 | |
| WO | WO 2006/048291 A2 | 5/2006 | |
| WO | WO 2006/113590 A2 | 10/2006 | |
| WO | WO 2006/119439 A2 | 11/2006 | |
| WO | WO 2007/015174 A2 | 2/2007 | |
| WO | WO 2007/103572 A2 | 9/2007 | |
| WO | WO 2007/126386 A1 | 11/2007 | |
| WO | WO 2007/127848 A1 | 11/2007 | |
| WO | WO 2008/084331 A2 | 7/2008 | |
| WO | WO 2008/104543 A2 | 9/2008 | |
| WO | WO 2009/015357 A1 | 1/2009 | |
| WO | WO 2009/021322 A1 | 2/2009 | |
| WO | WO 2009/030029 A1 | 3/2009 | |
| WO | WO 2009/036236 A1 | 3/2009 | |
| WO | WO 2009/092386 A2 | 7/2009 | |
| WO | 2009100029 A1 | 8/2009 | |
| WO | WO2009100029 * | 8/2009 | ............... C12Q 1/68 |
| WO | WO 2009/155505 A2 | 12/2009 | |
| WO | WO 2010/028099 A1 | 3/2010 | |
| WO | WO 2010/056337 A2 | 5/2010 | |
| WO | WO 2010/065968 A1 | 6/2010 | |
| WO | WO 2010/099184 A1 | 9/2010 | |
| WO | WO 2010/141955 A2 | 12/2010 | |
| WO | 2011009104 A1 | 1/2011 | |
| WO | WO2011009104 * | 1/2011 | ............. G01N 33/48 |
| WO | WO 2011/031877 A1 | 3/2011 | |
| WO | WO 2011/031892 A1 | 3/2011 | |
| WO | WO 2011/088226 A2 | 7/2011 | |
| WO | WO 2011/127219 A1 | 10/2011 | |
| WO | WO 2012/031008 A2 | 3/2012 | |
| WO | WO 2012/051622 A2 | 4/2012 | |
| WO | WO 2012/064993 A1 | 5/2012 | |

OTHER PUBLICATIONS

Michael A, Bajracharya SD, Yuen PS, Zhou H, Star Ra, Illei GG, Alevizos I. Exosomes from human saliva as a source of microRNA biomarkers. Oral Dis. Jan. 2010; 16(1):34-8. Epub Jul. 15, 2009. (Year: 2010).*

Pisitkun T, Shen RF, Knepper MA. Identification and proteomic profiling of exosomes in human urine. Proc Natl Acad Sci U S A. Sep. 7, 2004; 101(36):13368-73. Epub Aug. 23, 2004. (Year: 2004).*

Rood IM, Deegens JK, Merchant ML, Tamboer WP, Wilkey DW, Wetzels JF, Klein JB. Comparison of three methods for isolation of urinary microvesicles to identify biomarkers of nephrotic syndrome. Kidney Int. Oct. 2010; 78(8):810-6. Epub Aug. 4, 2010. (Year: 2010).*

Simpson RJ, Jensen SS, Lim JW. Proteomic profiling of exosomes: current perspectives. Proteomics. Oct. 2008; 8(19):4083-99. (Year: 2008).*

Fernandez-Llama P, Khositseth S, Gonzales PA, Star RA, Pisitkun T, Knepper MA. Tamm-Horsfall protein and urinary exosome isolation. Kidney Int. Apr. 2010; 77(8):736-42. Epub Feb. 3, 2010. (Year: 2010).*

Taylor DD, Shah S. Methods of isolating extracellular vesicles impact down-stream analyses of their cargoes. Methods. Oct. 1, 2015; 87:3-10. Epub Mar. 10, 2015. (Year: 2015).*

Thery C, Amigorena S, Raposo G, Clayton A. Isolation and characterization of exosomes from cell culture supernatants and biological fluids. Curr Protoc Cell Biol. Apr. 2006; Chapter 3: Unit 3.22, pp. 1-29. (Year: 2006).*

Alvarez ML, Khosroheidari M., Kanchi Ravi R. DiStefano JK. Comparison of protein, microRNA, and mRNA yields using different methods of urinary exosome isolation for the discovery of kidney disease biomakers. Kidney Int. Nov. 2012; 82(9): 1024-32. Epub Jul. 11, 2012.

Hunter MP, Ismail N, Zhang X, Aguda BD, Lee EJ, Yu L, Xiao T, Schafer J, Lee ML, Schmittgen TD, Nana-Sinkam SP, Jarjoura D, Marsh CB. Detection of microRNA expression in human peripheral blood microvesicles. PLoS One. 2008; 3(11):e3694. Epub Nov. 11, 2008.

Miranda KC, Bond DT, McKee M, Skog J, Paunescu Tg, Da Silva N, Brown D, Russo LM. Nucleic acids within urinary exosomes/microvesicles are potential biomarkers for renal disease. Kidney Int. Jul. 2010; 78(2): 191-9. Epub Apr. 28, 2010.

(56) References Cited

OTHER PUBLICATIONS

Michael A, Bajracharya SD, Yuen PS, Zhou H, Star RA, Illei GG, Alevizos I. Exosomes from human saliva as a source of microRNA biomarkers. Oral Dis. Jan. 2010; 16(1): 34-8. Epub Jul. 15, 2009.
Pisitkun T, Shen RF, Knepper MA. Identification and proteomic profiling of exosomes in human urine. Proc Natl Arad Sci USA. Sep. 7, 2004; 101(36): 13368-73. Epub Aug. 23, 2004.
Rood IM, Deegens JK, Merchant ML, Tamboer WP, Wilkey DW, Wetzels JF, Klein JB. Comparison of three methods for isolation of urinary microvesicles to identify biomakers of nephrotic syndrome. Kidney Int. Oct. 2010; 78(8): 810-6. Epub Aug. 4, 2010.
Simpson RJ, Jensen SS, Lim JW. Proteomic profiling of exosomes; current perspectives. Proteomics. Oct. 8, 2008 (19): 4083-99.
Valadi H, Ekstrom K, Bossios A, Sjostrand M, Lee JJ, Lotvall JO. Exosome-mediated transfer of mRNAs and nicroRNAs is a novel mechanism of genetic exchange between cells. Nat Cell Biol. Jun. 2007; 9(6): 654-9. Epub May 7, 2007.
Zhou H, Yuen PS, Pisitkun T, Gonzales PA, Yasuda H, Dear JW, Gross P, Knepper MA, Star RA Collection, storage, preservation, and normalization of human urinary exosomes for biomarker discovery. Kidney Int. Apr. 2006; 69(8): 1471-6.
Jacquillet G, Hoorn EJ, Vilasi A, Unwin RJ. Urinary Vesicles: In Splended Isolation. Nephrol Dial Transplant. Jun. 2013; 28(6):1332-5. Epub Jan. 24, 2013.
Abravaya, et al., "Detection of point mutations with a modified ligase chain reaction (Gap-LCR)." Nucleic Acids Research (1995); 23(4): 675-682.
Affymetriix, "GeneChip Human Genome U133 Set", Apr. 20, 2001, 2 pages, URL: http://www.affymetrix.com/products/arrays/specific/hgu_133_.asp.
Alessi et al., "New insights into mTOR signaling: mTORC2 and beyond", Sci Signal 2(67) pe27 (2009).
Allawi et al., "Quantitation of microRNAs using a modified Invader assay." RNA, 10:1153-1161 (2004).
Al-Nedawi, et al., "Intercellular transfer of the oncogenic receptor EGFRvIII by microvesicles derived from tumour cells." Nat Cell Biol. (2008); 10(5): 619-624.
Ason et al., "Differences in vertebrate microRNA expression." PNAS, 103(39):14385-14389 (2006).
Baj-Krzyworzeka et al., "Tumour-derived microvesicles carry several surface determinants and mRNA of tumour cells and transfer some of these determinants to monocytes." Cancer Immunology, Immunotherapy, 55(7):808-818 (2006).
Balzar, et al., "The biology of the 17-1A antigen (Ep-CAM)." J Mol Med. (1999); 77(10): 699-712.
Bamford et al., "The COSMIC (Catalogue of Somatic Mutations in Cancer) database and website", Br J Cancer 91 (2): 355-358 (2004).
Benner et al., "Evolution, language and analogy in functional genomics." Trends in Genetics, 17:414-418 (2001).
Bergsmedh et al., "Horizontal transfer of oncogenes by uptake of apoptotic bodies", Proc Natl Acad Sci USA 98(11) 5407-6411 (2001).
Biernat, et al., "Predominant Expression of Mutant Egfr (EGFRvIII) is Rare in Primary Glioblastomas." Brain Pathol (2004); 14: 131-136.
Booth et al., "Exosomes and hiv gag bud from endosome-like domains of the t cell plasma membrane." J Cell Biol., 172(6): 923-935 (2006). Published Online: Mar. 13, 2006.
Bossi et al., "Molecularly imprinted polymers for the recognition of proteins: The state of the art." Biosensors and Bioelectronics (2007); 22(6): 1131-1137.
Bratthauer et al., "Expression of LINE-1 retrotransposons in human breast cancer", Cancer 73(9) 2333-2336 (1994).
Burghoff et al., "Horizontal gene transfer from human endothelial cells to rat cardiomyocytes after intracoronary ransplantation", Cardiovasc Res 77(3) 534-543 (2008). online publish-ahead-of-print Nov. 13, 2007.
Cadieux et al., "Genome-wide hypomethylation in human glioblastomas associated with specific copy number alteration, methylenetetrahydrofolate reductase allele status, and increased proliferation", Cancer Res 66(17) 8469-8476 (2006).
Carr et al., "Circulating membrane vesicles in leukemic blood", Cancer Res 45(11 Pt 2) 5944-5951 (1985).
Cermelli et al., "Circulating microRNAs in patients with chronic hepatitis C and non-alcoholic fatty liver disease." PLoS ONE, 6(8):e23937 (2011).
Chaput et al., "The potential of exosomes in immunotherapy." Expert Opin Biol Ther., 5(6):737-747 (2005).
Chen et al., "Real-time quantification of microRNAs by stem-loop RT- PCR." Nucleic Acid Research, 33(20):e179 (2005).
Chen, et al., "Microfluidic isolation and transcriptome analysis of serum microvesicles." Lab Chip (2010); 10(4): 505-511.
Chen, et. al., "Characterization of microRNAs in serum: a novel class of biomarkers for diagnosis of cancer and other diseases." Cell Research (2008); 18: 997-1006.
Cheng et al., "Advances of AKT pathway in human oncogenesis and as a target for anti-cancer drug discovery", Curr Cancer Drug Targets 8(1) 2-6 (2008).
Cheruvanky, et al., "Rapid isolation of urinary exosomal biomarkers using a nanomembrane ultrafiltration concentrator." Am J Physiol Renal Physiol. (2007); 292: F1657-F1661.
Cheung et al., "Natural variation in human gene expression assessed in lymphoblastoid cells." Nature Genetics, 33:422-425 (2003).
Cho et al., "Hypermethylation of CpG island loci and hypomethylation of LINE-1 and Alu repeats in prostate adenocarcinoma and their relationship to clinicopathological features", J Pathol 211 (3) 269-277 (2007).
Choi, et al., "Proteomic Analysis of Microvesicles Derived from Human Colorectal Cancer Cells." Journal of Proteome Rsearch (2007); 6: 4646-4655.
Ciafrè et al., "Extensive modulation of a set of microRNAs in primary glioblastoma." Biochemical and Biophysical Research Communications, 334:1351-1358 (2005).
Clayton et al., "Human tumor-derived exosomes selectively impair lymphocyte responses to interleukin-2." Cancer Res., 67(15):7458-7466 (2007).
Cocucci, et al., "Shedding microvesicles: artefacts no more." Trends in Cell Biology (2009); 19 (2): 43-51.
Contreras-Galindo et al., "Human endogenous retrovirus K (HML-2) elements in the plasma of people with ymphoma and breast cancer", J Virol 82(19) 9329-9336 (2008).
Cooperberg, et al., "The Changing Face of Low-risk Prostate Cancer: Trends in Clinical Presentation and Primary Management." J Clin Oncolog (2004); 22 (11): 2141-2149.
Corsten et al., "Circulating MicroRNA-208b and MicroRNA-499 Reflect Myocardial Damage in Cardiovascular Disease." Circulation Cardiovascular Genetics, 2:499-506 (2010).
Cortez and Calin, "MicroRNA identification in plasma and serum: a new tool to diagnose and monitor diseases", Expert Opin Biol Ther 9(6) 703-711 (2009).
Cotton, et al., "Reactivity of cytosine and thymine in single-base-pair mismatches with hydroxylamine and osmium tetroxide and its application to the study of mutations." Proc Natl Acad Sci U S A (1988); 85 (12): 4397-4401.
Cowell et al., "Application of oligonucleotides arrays for coincident comparative genomic hybridization, ploidy status and loss of heterozygosity studies in human cancers", Methods Mol Biol 556: 47-65 (2009).
Daskalos et al., "Hypomethylation of retrotransposable elements correlates with genomic instability in non-small cell lung cancer." Int J Cancer 124(1) 81-87 (2009).
Day et al., "PCA3: from basic molecular science to the clinical lab", Cancer Lett 301(1) 1-6 (2011).
Deregibus et al., "Endothelial progenitor cell-derived microvesicles activate an angiogenic program in endothelial cells by a horizontal transfer of mRNA", Blood 110(7) 2440-2448 (2007).
Diehl et al., "BEAMing: single-molecule PCR on microparticles in water-in-oil emulsions", Nat Methods 3(7) 551-559 (2006).
Diehl et al., "Circulating mutant DNA to assess tumor dynamics." Nat Med., 14(9):985-999 (2008).

(56) References Cited

OTHER PUBLICATIONS

Dowling et al., "mTORC1-mediated cell proliferation, but not cell growth, controlled by the 4E-BPs", Science 328 (5982) 1172-1176 (2010).
Dressman et al., "Transforming single DNA molecules into fluorescent magnetic particles for detection and enumeration of genetic variations", Proc Nall Acad Sci USA 100(15) 8817-S822 (2003).
Duijvesz et al., "Exosomes as biomarker treasure chests for prostate cancer", Eur Urol 59(5) 823-831 (2011).
El-Hefnawy, et al., "Characterization of amplifiable, circulating RNA in plasma and its potential as a tool for cancer diagnostics." Clinical Chemistry, 50(3): 564-573 (2004).
Estécio et al., "Line-1 Hypomethylation in Cancer Is Highly Variable and Inversely Correlated with Microsatellite Instability", PLoS One 2(5) e399 (2007).
Extended European Search Report for European Patent Application No. 11839005.3, dated Mar. 27, 2014, 8 pages.
Fabbri et al., "MicroRNA-29 family reverts aberrant methylation in lung cancer by targeting DNA methyltransferases 3A and 3B." PNAS, 104(40):15805-15810 (2007).
Fiorentino et al., "The minisequencing method: an alternative strategy for preimplantation genetic diagnosis of single gene disorders", Mol Human Reprod 9(7) 399-410 (2003).
Fischer and Lerman, "[11] Two-dimensional electrophoretic separation of restriction enzyme fragments of DNA." Methods in Enzymology (1979); 68: 183-191.
Fischer and Lerman, "Length-independent separation of DNA restriction fragments in two-dimensional gel electrophoresis." Cell (1979); 16(1): 191-200.
Forbes et al., "COSMIC (the Catalogue of Somatic Mutations in Cancer): a resource to investigate acquired mutations in human cancer", Nucleic Acids Res 38(Database issue) D652-D657 (2010).
Forbes et al., "COSMIC: mining complete cancer genomes in the Catalogue of Somatic Mutations in Cancer", Nuclec Acids Res 39(Database issue) D945-D950 (2011).
Forbes et al., "The Catalogue of Somatic Mutations in Cancer (COSMIC)", Supplement 57:Unit-10.11, 32 pages (2008).
Furnari, et al., "Malignant astrocytic glioma: genetics, biology, and paths to treatment." Genes & Dev. (2007); 21: 2683-2710.
Gambim, et al., "Platelet-derived exosomes induce endothelial cell apoptosis through peroxynitrite generation: experimental evidence for a novel mechanism of septic vascular dysfunction", Crit Care 11 (5) R 107 (2007).
Geiss et al., "Direct multiplexed measurement of gene expression with color-coded probe pairs." Nat Biotechnol. (2008); 26 (3): 317-325.
GenBank (Accession NM_005896) submitted Jan. 31, 2003, 4 pages.
Ginestra et al., "The amount and proteolytic content of vesicles shed by human cancer cell lines correlates with their in vitro invasiveness." Anticancer Research, 18(5A): 3433-3437 (1998).
Golan et al., "Human endogenous retrovirus (HERV-K) reverse transcriptase as a breast cancer prognostic marker", Neoplasia 10(6) 521-533 (2008).
Gonzales, et. al., "Urinary exosomes: is there a future?" Nephrol Dial Transplant (2008); 23 (6): 1799-1801.
Goodier and Kazazian, Jr., "Retrotransposons Revisited: The Restraint and Rehabilitation of Parasites", Cell 135(1) 23-35 (2008).
Gormally et al., "Circulating free dna in plasma or serum as biomarker of carcinogenesis: practical aspects and biological significance." Mutat Res., 635:105-117 (2007).
Greco, et al., "Argosomes: a potential vehicle for the spread of morphogens through epithelia." Cell., 106 (5): 633-645 (2001).
Green et al., "The prognostic significance of IDH1 mutations in younger adult patients with acute myeloid leukemia is dependent on FLT3/ITD status", Blood 116(15) 277-2782 (2010).
Groskopf et al., "Aptima pca3 molecular urine test: development of a method to aid in the diagnosis of prostate cancer." Clin Chem., 52(6):1089-1095 (2006).

Guatelli, et al., "Isothermal, in vitro amplification of nucleic acids by a multienzyme reaction modeled after retroviral replication." Proc Natl Acad Sci U S A (1990); 87 (19): 1874-1878.
Guescini et al., "Astrocytes and Glioblastoma cells release exosomes carrying mtDNA", J Neural Transm (2010); 117(1) 1-4.
Hahn, "Molecular biology of double-minute chromosomes." BioEssays (1993); 15(7): 477-484.
Hanahan and Weinberg, "The hallmarks of cancer", Cell 100(1) 57-70 (2000).
Hartman et al., "Patients with IDH1 wild type anaplastic astrocytomas exhibit worse prognosis than IDH1-mutated glioblastomas, and IDH1 mutation status accounts for the unfavorable prognostic effect of higher age: implications for lassification of gliomas", Acta Neuropathol 120(6) 707-718 (2010).
Heimberger et al., "The natural history of EGFR and EGFRvIII in glioblastoma patients", J Transl Med 3: 38 (2005).
Hessels et al., "DD3PCA3-based Molecular Urine Analysis for the Diagnosis of Prostate Cancer." European Urology, 44:8-16 (2003).
Hessels, et. al., "Detection of TMPRSS2-ERG Fusion Transcripts and Prostate Cancer Antigen 3 in Urinary Sediments May Improve Diagnosis of Prostate Cancer." Clin Cancer Res (2007); 13 (17): 5103-5108.
Hildebrant et al., "Genetic variations in the PI3K/PTEN/AKT/mTOR pathway are associated with clinical outcomes in esophageal cancer patients treated with chemoradiotherapy", J Clin Oncol 27(6) 857-871 (2009).
Holdhoff et al., "Analysis of Circulating Tumor DNA to Confirm Somatic KRAS Mutations." J Natl Cancer Inst 101(18) 1284-1285 (2009).
Iero et al., "Tumour-released exosomes and their implications in cancer immunity." Cell Death and Differentiation, 15:80-88 (2008).
Iorio et al., "MicroRNA signatures in human ovarian cancer." Cancer Research, 67(18):8699-8707 (2007).
Itadani Et al., "Can systems biology understand pathway activation? Gene expression signatures as surrogate markers for understanding the complexity of pathway activation", Curr Genomics 9(5) 349-360 (2008).
Janowska-Wieczorek et al., "Microvesicles derived from activated platelets induce metastasis and angiogenesis in lung cancer." Int J Cancer., 113 (5): 752-760 (2005).
Ji et al., "MALAT-1, a novel noncoding RNA, and thymosin ß4 predict metastasis and survival in early-stage non-small cell lung cancer", Oncogene 22(39) 8031-8041 (2003).
Johnson et al., "Surface-immobilized peptide aptamers as probe molecules for protein detection." Anal Chem., 80:978-983 (2008).
Jones et al., "Core signaling pathways in human pancreatic cancers revealed by global genomic analyses." Science, 321(5897):1801-1806 (2008).
Kan and Dozy, "Antenatal diagnosis of sickle-cell anaemia by DNA analysis of amniotic-fluid cells." The Lancet (1978); 312(8096): 910-912.
Kan and Dozy, "Polymorphism of DNA sequence adjacent to human ß-globin structural gene: relationship to sickle mutation." PNAS (1978); 75(11): 5631-5635.
Kang et al., "Mutational analysis of IDH1 codon 132 in glioblastomas and other common cancers", Int J Cancer 125 (2) 353-355 (2009).
Kato et al., "A monoclonal antibody IMab-1 specifically recognizes IDH1R132H, the most common glioma-derived mutation", Biochem Biophys Res Commun 390(3) 547-551 (2009).
Katoh and Kurata, "Association of endogenous retroviruses and long terminal repeats with human disorders", Frontiers in Oncology (2013) 3 (234): 1-8.
Keller, et al., "CD24 is a marker of exosomes secreted into urine and amniotic fluid." Kidney Int. (2007); 72 (9): 1095-1102.
Keller, et al., "Exosomes: From biogenesis and secretion to biological function." Immunology Letters (2006); 107: 102-108.
Kislauskis et al., "Sequences Responsible for Intracellular Localization of ß-Actin Messenger RNA Also Affect Cell Phenotype." J Cell Biol., 127:441-451 (1994).
Kleiman et al., "HERV-K(HML-2) GAG/ENV antibodies as indicator for therapy effect in patients with germ cell tumors." Int J Cancer 110(3) 459-461 (2004).

(56) References Cited

OTHER PUBLICATIONS

Klein et al., "Combined transcriptome and genome analysis of single microstatic cells." Nature Biotechnology, 20:387-392 (2002).
Klemke et al., "Regulation of Cell Motility by Mitogen-activated Protein Kinase", J Cell Biol 137(2) 481-492 (1997).
Koga, et. al., "Purification, Characterization and Biological Significance of Tumor derived Exosomes." Anticancer Research (2005); 25 (6A): 3703-3708.
Kosaka et al., "Circulating microRNA in body fluid: a new potential biomarker for cancer diagnosis and prognosis", Cancer Sci 101(10) 2087-2092 (2010).
Kristensen and Hansen, "PCR-based methods for detecting single-locus DNA methylation biomarkers in cancer diagnostics, prognostics, and response to treatment", Clin Chem 55(8) 1471-1483 (2009).
Krupp, G., "Stringent RNA quality control using the Agilent 2100 bioanalyzer." Application note, Agilent Technologies, Feb. 1, 2005, 8 pages, retrieved from the Internet http://www.chem.agilent.com/library/applications/5989-1086en.pdf.
Kwoh, et al., "Transcription-based amplification system and detection of amplified human immunodeficiency virus type 1 with a bead-based sandwich hybridization format." Proc Natl Acad Sci U S A (1989); 86: 1173-1177.
Landegren, et al., "A ligase-mediated gene detection technique." Science (1988); 241(4869): 1077-1080.
Laxman et al., "A first-generation multiplex biomarker analysis of urine for the early detection of prostate cancer." Cancer Research, 68:645-649 (2008).
Lee et al., "Micro RNA expression and clinical outcome of small cell lung cancer." PLoS One, 6(6):e21300 (2011).
Li, et al., "BEAMing up for detection and quantification of rare sequence variants." Nat Methods. (2006); 3(2): 95-97.
Li, et al., "Replacing PCR with COLD-PCR enriches variant DNA sequences and redefines the sensitivity of genetic testing." Nature Medicine (2008); 14(5): 579-584.
Liu et al., "Murine Mammary Carcinoma Exosomes Promote Tumor Growth by Suppression of NK Cell Function." J Immunol., 176:1375-1385 (2006).
Liu, et al., "Reconstitution, activities, and structure of the eukaryotic RNA exosome." Cell (2006); 127 (6): 1223-1237.
Lo and Chiu, "Prenatal diagnosis: progress through plasma nucleic acids," Nat Rev Genet. (2007); 8 (1): 71-77.
Lo et al., "Plasma placental RNA allelic ratio permits noninvasive prenatal chromosomal aneuploidy detection." Nat Med., 13(2):218-223 (2007).
Lo, et al., "Automated gating offlow cytometry data via robust model-based clustering", Cytometry 73(4) 321-332 (2008).
Löower et al., "The viruses in all of us: Characteristics and biological significance of human endogenous retrovirus sequences", Proc Nall Acad Sci USA 93(11) 5177-5184 (1996).
Mack et al., "Transfer of the chemokine receptor CCR5 between cells by membrane-derived microparticles: a mechanism for cellular human immunodeficiency virus 1 infection." Nature Medicine, 6(7):769-775 (2000).
Maheswaran, et. al., "Detection of mutations in EGFR in circulating lung-cancer cells." N Engl J Med. (2008); 359 (4): 366-377.
Mallardo et al., "Isolation and characterization of Staufen-containing ribonucleoprotein particles from rat brain." Proc Natl Acad Sci USA, 100(4): 2100-2105 (2003).
Maron et al., "Gene expression analysis in pregnant women and their infants identifies unique fetal biomarkers that circulate in maternal blood." J Clin Invest., 117(10): 3007-3019 (2007).
Mellinghoff, et al., "Molecular Determinants of the Response of Glioblastomas to EGFR Kinase Inhibitors." The New England Journal of Medicine (2005); 353: 2012-2024.
Miele, et al., "Autocatalytic replication of a recombinant RNA." J Mol Biol. (1983); 171: 281-295.
Millimaggi et al., "Tumor vesicle-associated CD147 modulates the angiogenic capability of endothelial cells." Neoplasia 9(4):349-357 (2007).

Mitchell et al., "Can urinary exosomes act as treatment response markers in prostate cancer?", J Transl Med 7: 4 (2009).
Moscatello, et al., "Frequent Expression of a Mutant Epidermal Growth Factor Receptor in Multiple Human Tumors." Cancer Research (1995); 55: 5536-5539.
Myers, et al., "Detection of single base substitutions by ribonuclease cleavage at mismatches in RNA:DNA duplexes." Science (1985); 230(4731): 1242-1246.
Nagrath et al., "Isolation of rare circulating tumour cells in cancer patients by microchip technology." Nature, 450(7173): 1235-1239 (2007).
Nakanishi, et. al., "PCA3 Molecular Urine Assay Correlates With Prostate Cancer Tumor Volume: Implication in Selecting Candidates for Active Surveillance." The Journal of Urology (2008); 179 (5): 1804-1810.
Nakazawa, et al., "UV and skin cancer: specific p53 gene mutation in normal skin as a biologically relevant exposure measurement." Proc Natl Acad Sci U S A. (1994); 91: 360-364.
Ng et al., "mRNA of placental origin is readily detectable in maternal plasma." Proc Natl Acad Sci USA., 100(8):4748-4753 (2003).
Ng et al., "The concentration of circulating corticotropin-releasing hormone mRNA in maternal plasma is increased in preeclampsia." Clin Chem. 49(5):727-731 (2003).
Nilsson, et al., "Prostate cancer-derived urine exosomes: a novel approach to biomarkers for prostate cancer." British Journal of Cancer (2009); 100: 1603-1607.
Nishikawa et al., "Immunohistochemical analysis of the mutant epidermal growth factor, ΔEGFR, in glioblastoma." Brain Tumor Pathol 21(2) 53-56 (2004).
Noerholm et al., "RNA expression patterns in serum microvesicles from patients with glioblastoma multiforme and controls", BMC Cancer 12: 22 (2012).
Novakova et al., "MicroRNA involvement in glioblastoma pathogenesis", Biochem Biophys Res Commun 386(1) 1-5 (2009).
Oliveira et al., "Distinct patterns of KRAS mutations in colorectal carcinomas according to gerrnline mismatch repair defects and hMLH1 methylation status", Hum Mol Genet 13(19) 2303-2311 (2004).
Orita, et al., "Detection of polymorphisms of human DNA by gel electrophoresis as single-strand conformation polymorphisms." PNAS (1989); 86(8): 2766-2770.
Orozco and Lewis, "Flow cytometric analysis of circulating microparticles in plasma." Cytometry A (2010); 77A(6): 502-514.
Orozco, et al., "Membrane Protected Apoptotic Trophoblast Microparticles Contain Nucleic Acids." The Amerian Journal of Pathology (2008); 173 (6): 1595-1608.
Ostrowski et al., "Rab27a and Rab27b control different steps of the exosome secretion pathway", Nat Cell Biol 12 (1) 19-30 sup pp. 1-13 (2010).
Parsons et al., "An Integrated Genomic Analysis of Human Glioblastoma Multiforme." Science, 321(5897): 1807-1821 (2008).
PCT/US2011/060251, International Preliminary Report on Patentability, dated May 14, 2013, 7 pages.
PCT/US2011/060251, International Search Report and Written Opinion, dated Mar. 5, 2012, 9 pages.
Pelloski, et al., "Epidermal Growth Factor Receptor Variant III Status Defines Clinically Distinct Subtypes of Glioblastoma." Journal of Clinical Oncology (2007); 25(16): 2288-2294.
Pisitkun, et. al., "Discovery of urinary biomarkers." Mol Cell Proteomics (2006); 5 (10): 1760-1771.
Pleasance et al., "A comprehensive catalogue of somatic mutations from a human cancer genome", Nature 463 (7278) 191-196 (2010).
Rak et al., "Genetic determinants of cancer coagulopathy, angiogenesis and disease progression", Vnitr Lek 52(Suppl 1) 135-138 (2006).
Raposo, et al., "B lymphocytes secrete antigen-presenting vesicles." Journal of Experimental Medicine (1996); 183: 1161-1172.
Ratajczak et al., "Membrane-derived microvesicles: important and underappreciated mediators of cell-to-cell communication." Leukemia, 20:1487-1496 (2006).
Revenfeld et al., "Diagnostic and prognostic potential of extracellular vesicles in peripheral blood", Clin Ther 36(6) 830-846 (2014).

(56) References Cited

OTHER PUBLICATIONS

Roman-Gomez et al., "Repetitive DNA hypomethylation in the advanced phase of chronic myeloid leukemia", Leuk Res 32(3) 487-490 (2008).
Ruprecht et al., "Endogenous retroviruses and cancer." Cell Mol Life Sci 65(21) 3366-3382 (2008).
Ryan, et. al., "A prospective study of circulating mutant KRAS2 in the serum of patients with colorectal neoplasia: strong prognostic indicator in postoperative follow up." Gut (2003); 52:101-108.
Saal and Harvey, "MicroRNAs and the kidney: coming of age." Current Opinion in Nophrology and Hypertension, 18(4):317-323 (2009).
Sarbassov et al., "Prolonged rapamycin treatment inhibits mTORC2 assembly and Akt/PKB", Mol Cell 22(2) 159-168 (2006).
Schetter et al., "MicroRNA expression profiles associated with prognosis and therapeutic outcome in colon adenocarcinoma." JAMA, 299(4):425-436 (2008).
Shinojima et al., "Prognostic value of epidermal growth factor receptor in patients with glioblastoma multiforme", Cancer Res 63(20) 6962-6970 (2003).
Schmidt, et al., "QuantitativeMulti-Gene Expression Profiling of Primary Prostate Cancer." The Prostate (2006); 66: 1521-1534.
Simons and Raposo, "Exosomes—vesicular carriers for intercellular communication", Curr Opin Cell Biol 21 (4) 575-581 (2009).
Skog, et al., "Glioblastoma microvesicles transport RNA and proteins that promote tumour growth and provide diagnostic biomarkers." Nature Cell Biology (2008); 10(12): 1470-1476.
Sliva and Schnierle, "Selective gene silencing by viral delivery of short hairpin RNA", Virol J 7: 248 (2010).
Srikantan et al., "PCGEM1, a prostate-specific gene, is overexpressed in prostate cancer", Proc Nall Acad Sci USA 97(22) 12216-12221 (2000).
Steemers, et al., "Whole-genome genotyping with the single-base extension assay." Nature Methods (2006); 3: 31-33.
Stoorvogel, et al., "The Biogenesis and Functions of Exosomes." Traffic (2002); 3 (5): 321-330.
Tam, W., "The emergent role of microRNAs in molecular diagnostics of cancer." J Mol Diagn (2008); 10 (5):411-144.
Taylor and Gercel-Taylor, "MicroRNA signatures of tumor-derived exosomes as diagnostic biomarkers of ovarian cancer." Gynecol Oncol. (2008); 110: 13-21.
Taylor and Gerçel-Taylor, "Tumour-derived exosomes and their role in cancer-associated T-cell signalling defects." British Journal of Cancer, 92 (2): 305-3011 (2005).
Tewes, et. al., "Molecular profiling and predictive value of circulating tumor cells in patients with metastatic breast cancer: an option for monitoring response to breast cancer related therapies." Breast Cancer Res Treat (2009); 115 (3): 581-590.
The Cancer Genome Atlas (TCGA) Research Network, "Comprehensive genomic characterization defines human glioblastoma genes and core pathways", Nature 455(7216) 1061-1068 (2008).
Théry et al., "Isolation and characterization of exosomes from cell culture supernatants and biological fluids." Curr Protoc Cell Biol. Chapter 3:Unit 3 22.1-3.22.29, (2006).
Théry, et al., "Exosomes: composition, biogenesis and function." Nature Reviews Immunology (2002); 2 (8): 569-579.
Ting et al., "Aberrant overexpression of satellite repeats in pancreatic and other epithelial cancers", Science 331 (6017) 593-596 (2011).
Tomlins et al., "Recurrent fusion of TMPRSS2 and ETS transcription factor genes in prostate cancer", Science 310 (5748) 644-648 (2005).
Van Dijk, et al., "Human cell growth requires a functional cytoplasmic exosome, which is involved in various mRNA decay pathways." RNA (2007); 13: 1027-1035.
Velculescu, et al., "Serial Analysis of Gene Expression." Science (1995); 270(5235): 484-487.
Voisset et al., "Human RNA "Rumor" Viruses: the Search for Novel Human Retroviruses in Chronic Disease." Microbiol Mol Biol Rev 72(1) 157-196 (2008).
Wang-Johanning et al., "Human endogenous retrovirus K triggers an antigen-specific immune response in breast cancer patients", Cancer Res 68(14) 5869-5877 (2008).
Went et al., "Frequent epcam protein expression in human carcinomas." Hum Pathol., 35:122-128 (2004).
Wieckowski and Whiteside, "Human tumor-derived vs dendritic cell-derived exosomes have distinct biologic roles and molecular profiles." Immunol Res., 36(1-3):247-254 (2006).
Wong et al., "Circulating placental RNA in maternal plasma is associated with a preponderance of 5' mRNA fragments: implications for noninvasive prenatal diagnosis and monitoring." Clin Chem., 51(10):1786-1795 (2005).
Wood et al., "The genomic landscapes of human breast and colorectal cancers." Science, 318:1108-1113 (2007).
Wright and Lange, "Newer potential biomarkers in prostate cancer", Rev Urol 9(4) 207-213 (2007).
Yan et al., "1DH1 and 1DH2 mutations in gliomas", N Engl J Med 360(8) 765-773 (2009).
Yoshimoto et al., "Development of a real-lime RT-PCR assay for detecting EGFRvIII in glioblastoma samples", Clin Cancer Res 14(2) 488-493 (2008).
Yu and Rak, "Shedding of tissue factor (TF)-containing microparticles rather than alternatively spliced TF is the main source of TF activity released from human cancer cells." Journal of Thrombosis and Haemostatis (2004); 2 (11): 2065-2067.
Yu et al., "Oncogenic events regulating tissue factor expression." Haematological Reports, 1(9):18-20 (2005).
Yuan et al., "Transfer of MicroRNAs by Embryonic Stem Cell Microvesicles." PLoS One 4(3) e4772 (2009).
Bess, et al., "Microvesicles are a source of contaminating cellular proteins found in purified HIV-1 preparations." Virology (Mar. 1997); 230(1):134-44.
Chabert, et al., "Cell culture of tumors alters endogenous poly(ADPR)polymerase expression and activity", Int J Cancer (1993); 53(5): 837-842.
Choi, et al., "Proteomic analysis of microvesicles derived from human colorectal cancer ascites." Proteomic (2011); 11 (13): 2745-2751.
Dermer, "Another anniversary for the war on cancer." Nature Biotechnology 12(3):320 (1994).
Diehl, et al., "Detection and quantification of mutations in the plasma of patients with colorectal tumors." PNAS (2005); 102(45): 16268-16373.
Eastham, et al., "Relationship between clonogenic cell survival, DNA damage and chromosomal radiosensitivity in nine human cervix carcinoma cell lines" Int. Journal Radial. Biol (2001); 77(3): 295-302.
Grant, et al., "The Proteins of Normal Urine." The Proteins of Normal Urine Journal of Clinical Pathology 1957;10: 360-368.
May, "How Many Species Are there on Earth?" Science 241(1) 1441-1449 (1998).
Modrek, et al., "Genome-wide detection of alternatives splicing in expressed sequences of human genes", Nucleic Acids Research 29(13) 2850-2859 (2001).
Ruprecht, et al., "Human endogenous retrovirus family HERV-K(HML-2) RNA transcripts are selectively packaged into retroviral particles produced by the human germ cell tumor line Tera-1 and originate mainly from a provirus on chromosome 22q11.21" J Virol 82(20) 10008-10016 (2008).
Saito-Hisaminto, et al., "Genome-Wide Profiling of Gene Expression in 29 Normal Human Tissues with cDNA Microarray", DNA Research (2002); 9: 35-45.
Silva, et al., "Selective gene silencing by viral delivery of short hairpin RNA", Virol J 7: 248 (2010).
Singh, et al., "Gene Expression correlates of clinical prostate cancer behavior", Cancer Cell (2002); 1 (2): 203-209.
The International SNP Map Working Group., "A map of human genome sequence variation containing 1.42 million ingle nucleotide polymorphisms" Nature (2001); 409: 928-933.

(56) References Cited

OTHER PUBLICATIONS

Tullis, et al., "Calcium protects DNase I from proteinase K: a new method for the removal of contaminating RNase from DNase I." Anal Biochem. (1980); 107(1): 260-264.

* cited by examiner

METHOD FOR ISOLATION OF NUCLEIC ACID CONTAINING PARTICLES AND EXTRACTION OF NUCLEIC ACIDS THEREFROM

CROSS REFERENCE TO RELATED APPLICATIONS

This application is a continuation of U.S. application Ser. No. 13/883,673, which is a national stage application, filed under 35 USC § 371, of PCT Application No. PCT/US2011/060251, filed Nov. 10, 2011, which claims priority to U.S. provisional application No. 61/412,369, filed Nov. 10, 2010, the contents of each of which are incorporated herein by reference in their entireties.

FIELD OF INVENTION

The present invention relates to the general fields of nucleic acid extraction from a biological sample, particularly the isolation of nucleic acid-containing particles from body fluids and extraction of nucleic acids from the isolated particles.

BACKGROUND

Small microvesicles shed by cells are often described as "exosomes" (Thery et al., 2002). Exosomes are reported as having a diameter of approximately 30-100 nm and are shed from many different cell types under both normal and pathological conditions (Thery et al., 2002). Exosomes are classically formed from the inward invagination and pinching off of the late endosomal membrane. This results in the formation of a multivesicular body (MVB) laden with small lipid bilayer vesicles, each of which contains a sample of the parent cell's cytoplasm (Stoorvogel et al., 2002). Fusion of the MVB with the cell membrane results in the release of these exosomes from the cell, and their delivery into the blood, urine, cerebrospinal fluid, or other bodily fluids.

Another category of cell-derived microvesicles are formed by directly budding off of the cell's plasma membrane, are usually larger in size than exosomes, and like exosomes, also contain a sample of the parent cell's cytoplasm (Cocucci et al., 2009) (Orozco and Lewis, 2010).

Recent studies reveal that nucleic acids within microvesicles have a role as biomarkers. For example, WO 2009/100029 describes, among other things, the use of nucleic acids extracted from microvesicles in GBM patient serum for medical diagnosis, prognosis and therapy evaluation. WO 2009/100029 also describes the use of nucleic acids extracted from microvesicles in human urine for the same purposes. The use of nucleic acids extracted from microvesicles is considered to potentially circumvent the need for biopsies, highlighting the enormous diagnostic potential of microvesicle biology (Skog et al., 2008).

Several methods of isolating microvesicles from a biological sample have been described in the art. For example, a method of differential centrifugation is described in a paper by Raposo et al. (Raposo et al., 1996), a paper by Skog et. al. (Skog et al., 2008) and a paper by Nilsson et. al. (Nilsson et al., 2009). Methods of anion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in a paper by Taylor and Gercel-Taylor (Taylor and Gercel-Taylor, 2008). A method of nanomembrane ultrafiltration concentration is described in a paper by Cheruvanky et al. (Cheruvanky et al., 2007). A method of Percoll gradient isolation is described in a publication by Miranda et. al (Miranda et al., 2010). Further, microvesicles may be identified and isolated from bodily fluid of a subject by a microfluidic device (Chen et al., 2010).

In research and development, as well as commercial applications of nucleic acid biomarkers, it is desirable to extract high quality nucleic acids from biological samples in a consistent, reliable, and practical manner. An object of the present invention is therefore to provide a method for quick and easy isolation of nucleic acid-containing particles from biological samples such as body fluids and extraction of high quality nucleic acids from the isolated particles. The method of the invention may be suitable for adaptation and incorporation into a compact device or instrument for use in a laboratory or clinical setting, or in the field.

SUMMARY

The present invention is based on our discovery that low speed centrifugation can be used to pellet particles from a biological sample and extract high quality nucleic acids from the particles. In one aspect, the invention is a method for extracting nucleic acids by isolating nucleic acid-containing particles from a biological sample by one or more centrifugation procedures at a speed not exceeding about 200,000 g, performing one or more steps to mitigate adverse factors that prevent or might prevent high quality nucleic acid extraction; and extracting nucleic acids from the isolated particles.

In some embodiments, the centrifugation procedures are performed at speeds of about 2,000 g to about 200,000 g. In other embodiments, the centrifugation procedures are performed at speeds not exceeding about 50,000 g. In still other embodiments, the centrifugation procedures are performed at speeds not exceeding about 20,000 g. In some embodiments, the method is used to extract nucleic acids from microvesicles, RNA-protein complexes, DNA-protein complexes, or a combination of any of microvesicles, RNA-protein complexes, and DNA-protein complexes.

In some embodiments, the biological sample is a body fluid, for example, a serum or a urine sample from a subject. The subject, for example, can be a human or other mammal. The extracted nucleic acids can be RNA, DNA, or both RNA and DNA. In some further embodiments, the nucleic acids thus extracted contain one or more polynucleotides which are more than 90% homologous to a nucleic acid sequence corresponding to EGFR, BRAF, KLK3, 18S, GAPDH, HPRT1, GUSB, ACTB, B2M, RPLP0, HMBS, TBP, PGK1, IJBC, PPIA, ALCAM, C5AR1, CD160, CD163, CD19, CD1A, CD1C, CD1D, CD2, CD209, CD22, CD24, CD244, CD247, CD28, CD37, CD38, CD3D, CD3G, CD4, CD40, CD40LG, CD5, CD6, CD63, CD69, CD7, CD70, CD72, CD74, CD79A, CD79B, CD80, CD83, CD86, CD8A, CD8B, CD96, CHST10, COL1A1, COL1A2, CR2, CSFIR, CTLA4, DPP4, ENG, FAS, FCER1A, FCER2, FCGR1A/FCGR1B/FCGR1C, HLA-A/HLA-A29.1, HLA-DRA, ICAM2, IL12RB1, IL1R2, IL2RA, ITGA1, ITGA2, ITGA3, KLRB1, KLRC1, KLRD1, KRT18, KRT5, KRT8/LOC728638, MS4A1, MYH10, MYH9, MYOCD, NCAM1, NOS3, NT5E, PECAM1, RETN, S100A8, SELP, ST6GAL1, EPCAM, TEK, TNFRSF4, TNFRSF8, TPSAB1/TPSB2, VCAM1, or VWF.

In some embodiments, 18S rRNA and 28S rRNA are detectable in the extracted nucleic acids. In some instances, the ratio of the amount of 18S rRNA to the amount of 28S rRNA as detected in the extracted nucleic acids is about 0.5 to about 1.0. In other instances, the ratio of the amount of 18S rRNA to the amount of 28S rRNA as detected in the extracted nucleic acids is about 0.5.

In some embodiments, the step of performing one or more steps to mitigate adverse factors is achieved by treating the biological sample and/or the isolated particles with DNase, RNase inhibitor, or both DNase and RNase inhibitors. In certain embodiments, the step of performing one or more steps to mitigate adverse factors is achieved by a step of treating the biological sample with RNase inhibitor before isolating the particles.

In another aspect, the present invention is a nucleic acid sample obtained from a biological sample by the any of above described methods. The nucleic acid sample thus obtained can be used in various applications. In some embodiments, the above method and resulting nucleic acid sample are used for aiding in the diagnosis of a subject by determining the presence or absence of a biomarker within the nucleic acid sample that is associated with a known disease or other medical condition. In other embodiments, the above method and resulting nucleic acid sample are used for monitoring the progress or reoccurrence of a disease or other medical condition in a subject by determining the presence or absence of a biomarker with in the sample that is associated with the progress or reoccurrence of a known stage or the reoccurrence of a disease or other medical condition. In still other embodiments, the above method and resulting nucleic acid sample are used in the evaluation of treatment efficacy for a subject undergoing or contemplating treatment for a disease or other medical condition by determining the presence or absence of a biomarker within the sample that is associated with treatment efficacy for the subject undergoing or contemplating treatment for a disease or other medical condition.

In some further embodiments, the biomarker detected in the above applications is a nucleic acid corresponding to any one or more of the genes consisting of EGFR, BRAF, KLK3, 18S, GAPDH, HPRT1, GUSB, ACTB, B2M, RPLP0, HMBS, TBP, PGK1, UBC, PPIA, ALCAM, C5AR1, CD160, CD163, CD19, CD1A, CD1C, CD1D, CD2, CD209, CD22, CD24, CD244, CD247, CD28, CD37, CD38, CD3D, CD3G, CD4, CD40, CD40LG, CD5, CD6, CD63, CD69, CD7, CD70, CD72, CD74, CD79A, CD79B, CD80, CD83, CD86, CD8A, CD8B, CD96, CHST10, COL1A1, COL1A2, CR2, CSF1R, CTLA4, DPP4, ENG, FAS, FCER1A, FCER2, FCGR1A/FCGR1B/FCGR1C, HLA-A/HLA-A29.1, HLA-DRA, ICAM2, IL12RB1, IL1R2, IL2RA, ITGA1, ITGA2, ITGA3, KLRB1, KLRC1, KLRD1, KRT18, KRT5, KRT8/LOC728638, MS4A1, MYH10, MYH9, MYOCD, NCAM1, NOS3, NT5E, PECAM1, RETN, S100A8, SELP, ST6GAL1, EPCAM, TEK, TNFRSF4, TNFRSF8, TPSAB1/TPSB2, VCAM1, and VWF.

Yet another aspect of the invention is a kit for use in the above methods. The kit may include RNase inhibitor in a quantity sufficient to mitigate adverse factors that prevent or might prevent high quality nucleic acid extraction, and an RNA purification reagent. The kit may optionally further include a lysis buffer, DNase, or instructions for using the kit and reagent in it in the extraction of nucleic acids from isolated particles.

DETAILED DESCRIPTION OF THE INVENTION

Figure 1A:
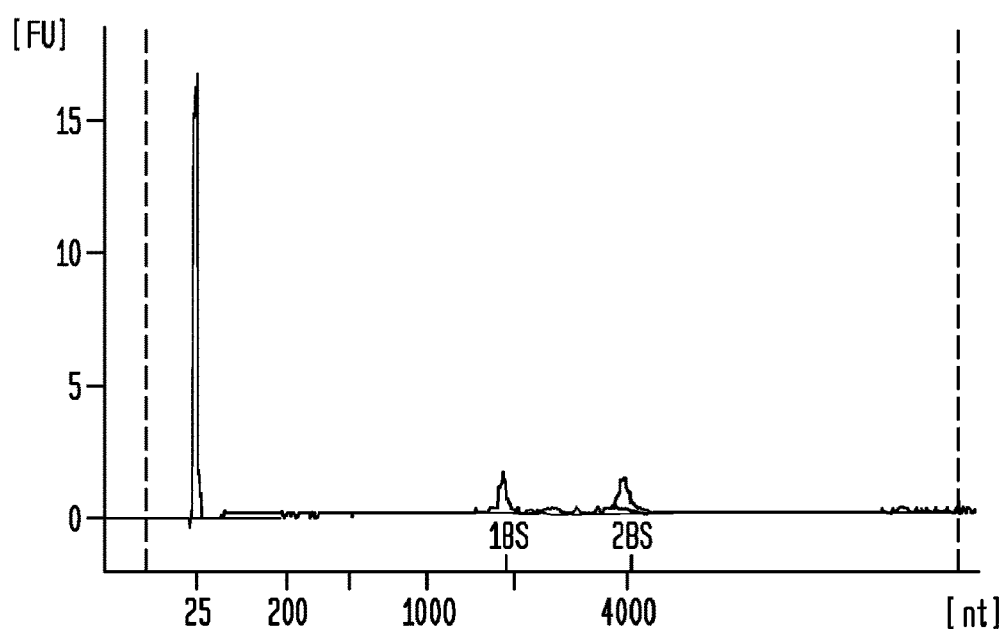
FIGS. 1A, 1B and 1C are Bioanalyzer plots depicting the analysis of nucleic acids extracted from particles isolated from serum samples as described in Examples 1, 2 and 3, respectively. The pseudogel in FIG. 1A depicts the content of the same nucleic acid extraction as depicted in the Bioanalyzer plot of FIG. 1A. The plots and the pseudogel were generated by an RNA pico chip run on an Agilent Bioanalyzer.

As described above, cell-derived vesicles are heterogeneous in size with diameters ranging from about 10 nm to about 5000 nm. For example, "exosomes" have diameters of approximately 30 to 100 nm, with shedding microvesicles and apoptotic bodies often described as larger (Orozco and Lewis, 2010). Exosomes, shedding microvesicles, microparticles, nanovesicles, apoptotic bodies, nanoparticles and membrane vesicles co-isolate using various techniques and will, therefore, collectively be referred to throughout this specification as "microvesicles" unless otherwise expressly denoted.

Other nucleic acid-containing particles, e.g., RNA-protein complexes and DNA-protein complexes, may co-isolate with microvesicles using the various methods and techniques described herein. Accordingly, the generic term "particles" will be used herein to refer to microvescles, RNA-protein complexes, DNA-protein complexes, and any other nucleic acid-containing particles that could be isolated according to the methods and techniques described herein. The methods and techniques described herein are equally applicable to the isolation of RNA-protein complexes, DNA-protein complexes, or other nucleic acid-containing particles, and microvesicles of all sizes (either as a whole, as select subsets, or as individual species).

The present invention is partly based on the discovery that lower centrifugation speeds can achieve similar results as higher centrifugation speeds during nucleic acid-containing particle isolation. As such, in one aspect, the present invention is directed to novel methods for isolating particles from a biological sample and extracting nucleic acids from the isolated particles. The nucleic acid extractions obtained by the methods described herein may be useful for various applications in which high quality nucleic acid extractions are required or preferred.

As used herein, the term "high quality" in reference to nucleic acid extraction means an extraction in which one is able to detect 18S and 28S rRNA, preferably in a ratio of approximately 1:1 to approximately 1:2; and more preferably, approximately 1:2. Ideally, high quality nucleic acid extractions obtained by the methods described herein will also have an RNA integrity number of greater than or equal to 5 for a low protein biological sample (e.g., urine), or greater than or equal to 3 for a high protein biological sample (e.g., serum), and a nucleic acid yield of greater than or equal to 50 pg/ml from a 20 ml low protein biological sample or a 1 ml high protein biological sample.

High quality RNA extractions are desirable because RNA degradation can adversely affect downstream assessment of the extracted RNA, such as in gene expression and mRNA analysis, as well as in analysis of non-coding RNA such as small RNA and microRNA. The new methods described herein enable one to extract high quality nucleic acids from particles isolated from a biological sample so that an accurate analysis of nucleic acids within the particles can be carried out.

Broadly described, the novel methods include, for example, the steps of obtaining a biological sample; isolating nucleic acid-containing particles from the biological sample by one or more centrifugation steps; mitigating or removing adverse factors that prevent high quality extraction of nucleic acids from the sample; and extracting nucleic acids from the isolated particles; followed, optionally, by nucleic acid analysis. The centrifugation step or steps may be performed at relatively low speeds as compared to traditional methods of isolating particles from biological samples by centrifugation. None of the centrifugation steps in the inventive methods described herein may exceed about 200,000 g.

Suitable centrifugation speeds are up to about 200,000 g; for example from about 2,000 g to less than about 200,000 g. Speeds of above about 15,000 g and less than about 200,000 g or above about 15,000 g and less than about 100,000 g or above about 15,000 g and less than about 50,000 g are preferred. Speeds of from about 18,000 g to about 40,000 g or about 30,000 g; and from about 18,000 g to about 25,000 g are more preferred. Particularly preferred is a centrifugation speed of about 20,000 g.

The methods described herein may be used with a variety of commercially available centrifuge machines and for the purpose of isolating various species of particles. A person of skill in the art will be able to use the well known K-factor to optimize the centrifugation parameters for a particular centrifuge device selected for use in the method. For example, the K-factor, which denotes the clearing factor of a centrifuge rotor at maximum rotation speed, may be used to determine the time ("T") required for pelleting a fraction with a known sedimentation coefficient ("S"). The lower the K-factor, the more efficient the pelleting with any given centrifuge device. The K-factor can be calculated by the following formula:

$$K = 2.53 * 10^{11} * \ln(r_{max}/r_{min})/RPM^2,$$

wherein $r_{max}$ is the maximum radius from the centrifuge's axis of rotation, and $r_{min}$ is the minimum radius from the axis of rotation. The $r_{max}$ and $r_{min}$ are usually available from the centrifuge manufacturer. RPM is the speed in revolutions per minute. The K-factor is related to the sedimentation coefficient S by the formula:

$$T = K/S,$$

where T is the time to pellet a certain particle in hours. Where S is a known constant for a certain particle, this relationship can be used to interconvert between different rotors using the following formula:

$$T_1/K_1 = T_2/K_2,$$

where $T_1$ is the time to pellet in one rotor, and $K_1$ is the K-factor of that rotor, $K_2$ is the K-factor of the other rotor, and $T_2$, the time to pellet in the other rotor. If one knows $K_1$, $T_1$, and can calculate $K_2$, then $T_2$ may be determined. In this manner, one does not need access to the exact centrifuge rotor cited in a particular protocol, as long as the K-factor can be calculated. If the sedimentation constant (S) is unknown for a particular substance to be pelleted, then one of skill in the art may determine $T_2$ based on empirical data as to $T_1$ for the same substance and calculation of $K_2$ for the different rotor.

Generally, suitable K factors are within the range of about 300 to about 1000; preferably within the range of about 400 to about 600; and more preferably about 520.

Generally, suitable times for centrifugation are from about 5 minutes to about 2 hours, for example, from about 10 minutes to about 1.5 hours, or more preferably from about 15 minutes to about 1 hour. A time of about 0.5 hours is sometimes preferred.

It is sometimes preferred to subject the biological sample to centrifugation at about 20,000 g for about 0.5 hours. However the above speeds and times can suitably be used in any combination (e.g., from about 18,000 g to about 25,000 g, or from about 30,000 g to about 40,000 g for about 10 minutes to about 1.5 hours, or for about 15 minutes to about 1 hour, or for about 0.5 hours, and so on).

The centrifugation step or steps may be carried out at below-ambient temperatures, for example at about 0-10° C., preferably about 1-5° C., e.g., about 3° C. or about 4° C.

As used herein, the term "biological sample" refers to a sample that contains biological materials such as a DNA, a RNA and a protein. In some embodiments, the biological sample may suitably comprise a bodily fluid from a subject. The bodily fluids can be fluids isolated from anywhere in the body of the subject, preferably a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof. In some embodiments, the preferred body fluid for use as the biological sample is urine. In other embodiments, the preferred body fluid is serum. In still other embodiments, the preferred body fluid is cerebrospinal fluid.

Suitably a sample volume of about 0.1 ml to about 30 ml fluid may be used. The volume of fluid may depend on a few factors, e.g., the type of fluid used. For example, the volume of serum samples may be about 0.1 ml to about 2 ml, preferably about 1 ml. The volume of urine samples may be about 10 ml to about 30 ml, preferably about 20 ml.

The term "subject" is intended to include all animals shown to or expected to have nucleic acid-containing particles. In particular embodiments, the subject is a mammal, a human or nonhuman primate, a dog, a cat, a horse, a cow, other farm animals, or a rodent (e.g. mice, rats, guinea pig, etc.). A human subject may be a normal human being without observable abnormalities, e.g., a disease. A human subject may be a human being with observable abnormalities, e.g., a disease. The observable abnormalities may be observed by the human being himself, or by a medical professional. The term "subject", "patient", and "individual" are used interchangeably herein.

The biological sample may be pre-processed before isolating nucleic acid-containing particles. In some instances, a pre-processing step is preferred. For example, a urine sample may be pre-processed to obtain urinary nucleic acid-containing particles. The pre-processing may be achieved by techniques known in the art such as differential centrifugation or filtration. For example, urine samples may undergo a first centrifugation step of about 300 g to get rid of large particles and debris in the samples. Urine samples may then undergo a second centrifugation step of about 5,000 g to about 20,000 g (larger volume centrifuged-higher k-factor) to get rid of unwanted particles that did not pellet in the previous centrifugation step, but without pelleting nucleic acid-containing particles that are desired in the final analysis. After the second centrifugation step, urine samples may further undergo a filtration step, e.g., 0.8 µm, 0.45 µm, or 0.22 µm filtration step to further rid the sample of unwanted materials. Alternatively, urine samples may be pre-processed by a filtration step without first undergoing the one or more of the centrifugation steps.

Generally therefore the biological sample may be pre-processed by centrifuging at a low speed of about 100-500 g, preferably about 250-300 g, to remove large unwanted particles and debris in the sample. Alternatively or additionally the biological sample may be pre-processed by centrifuging at a higher speed of about 10,000-20,000 g, preferably 15,000-19,000 g, to remove unwanted particles and substances in the sample. Where both centrifugation pre-processing steps are performed, the biological sample may be centrifuged first at the lower speed and then at the higher speed. If desired, further suitable centrifugation pre-processing steps may be carried out. For example, the step of centrifugation may be repeated for further pre-processing the samples. Alternatively or in addition to the one or more centrifugation pre-processing steps, the biological sample may be filtered. A filter having a size in the range about 0.1 to about 1.0 µm may be employed, preferably about 0.5 to about 1.0 µm, e.g. about 0.7 µm or about 0.8 µm.

The isolation step is advantageous for the extraction of high quality nucleic acids from a biological sample for the following reasons: 1) extracting nucleic acids from particles provides the opportunity to selectively analyze disease- or tumor-specific nucleic acids, which may be obtained by isolating disease- or tumor-specific particles apart from other particles within the fluid sample; 2) nucleic acid-containing particles such as microvesicles produce significantly higher yields of nucleic acid species with higher integrity as compared to the yield/integrity obtained by extracting nucleic acids directly from the fluid sample without first isolating microvesicles; 3) scalability, e.g. to detect nucleic acids expressed at low levels, the sensitivity can be increased by pelleting more nucleic acid-containing particles from a larger volume of serum; 4) purer nucleic acids in that protein and lipids, debris from dead cells, and other potential contaminants and PCR inhibitors are excluded from the pellets before the nucleic acid extraction step; and 5) more choices in nucleic acid extraction methods as pellets are of much smaller volume than that of the starting serum, making it possible to extract nucleic acids from these pellets using small volume column filters.

In one embodiment, the method of isolating particles from a body fluid and extracting nucleic acids from the isolated particles may comprise the steps of: removing cells from the body fluid either by low speed centrifugation and/or filtration though a 0.8 µm filter; centrifuging the supernatant/filtrate at about 20,000 g for about 0.5 hour at about 4° C. using about 1 ml sample volume; treating the pellet with a pre-lysis solution, e.g., an RNase inhibitor and/or a pH buffered solution and/or a protease enzyme in sufficient quantities (as described below); and lysing the pellet for nucleic acid extraction. In one embodiment, the process of isolating particles and extracting high quality nucleic acids may be achieved within 90 minutes.

Following isolation, nucleic acid may be extracted from the pelleted particles. To achieve this, in some embodiments, the particles may first be lysed. The lysis of particles such as microvesicles in the pellet and extraction of nucleic acids may be achieved with various methods known in the art. In one embodiment, the lysis and extraction steps may be achieved using a commercially available Qiagen RNeasy Plus kit. In another embodiment, the lysis and extraction steps may be achieved using a commercially available Qiagen miRNeasy kit. In yet another embodiment, the nucleic acid extraction may be achieved using phenol:chloroform according to standard procedures and techniques known in the art.

According to the present invention, the novel nucleic acid extraction methods include the step of removing or mitigating adverse factors that prevent high quality nucleic acid extraction from a biological sample. Such adverse factors are heterogeneous in that different biological samples may contain various species of adverse factors. In some biological samples, factors such as excessive DNA may affect the quality of nucleic acid extractions from such samples. In other samples, factors such as excessive endogenous RNase may affect the quality of nucleic acid extractions from such samples. Many agents and methods may be used to remove these adverse factors. These methods and agents are referred to collectively herein as an "extraction enhancement operations."

In some instances, the extraction enhancement operation may involve the addition of nucleic acid extraction enhancement agents to the biological sample. To remove adverse factors such as endogenous RNases, such extraction enhancement agents as defined herein may include, but are not limited to, an RNase inhibitor such as Superase-In (commercially available from Ambion Inc.) or RNaseINplus (commercially available from Promega Corp.), or other agents that function in a similar fashion; a protease (which may function as an RNase inhibitor); DNase; a reducing agent; a decoy substrate such as a synthetic RNA and/or carrier RNA; a soluble receptor that can bind RNase; a small interfering RNA (siRNA); an RNA binding molecule, such as an anti-RNA antibody, a basic protein or a chaperone protein; an RNase denaturing substance, such as a high osmolarity solution, a detergent, or a combination thereof. These enhancement agents may exert their functions in various ways, e.g., through inhibiting RNase activity (e.g., RNase inhibitors), through a ubiquitous degradation of proteins (e.g., proteases), or through a chaperone protein (e.g., a RNA-binding protein) that binds and protects RNAs. In all instances, such extraction enhancement agents remove or at least mitigate some or all of the adverse factors in the biological sample or associated with the isolated particles that would otherwise prevent or interfere with the high quality extraction of nucleic acids from the isolated particles.

For example, the extraction enhancement operation may include the addition of an RNase inhibitor to the biological sample, and/or to the isolated particle fraction, prior to extracting nucleic acid; preferably the RNase inhibitor has a concentration of greater than 0.027 AU (1×) for a sample equal to or more than 1 µl in volume; alternatively, greater than or equal to 0.135 AU (5×) for a sample equal to or more than 1 µl; alternatively, greater than or equal to 0.27 AU (10×) for a sample equal to or more than 1 µl; alternatively, greater than or equal to 0.675 AU (25×) for a sample equal to or more than 1 µl; and alternatively, greater than or equal to 1.35 AU (50×) for a sample equal to or more than 1 µl; wherein the 1× concentration refers to an enzymatic condition wherein 0.027 AU or more RNase inhibitor is used to treat particles isolated from 1 µl or more bodily fluid, the 5× concentration refers to an enzymatic condition wherein 0.135 AU or more RNase inhibitor is used to treat particles isolated from 1 µl or more bodily fluid, the 10× protease concentration refers to an enzymatic condition wherein 0.27 AU or more RNase inhibitor is used to treat particles isolated from 1 µl or more bodily fluid, the 25× concentration refers to an enzymatic condition wherein 0.675 AU or more RNase inhibitor is used to treat particles isolated from 1 µl or more bodily fluid, and the 50× protease concentration refers to an enzymatic condition wherein 1.35 AU or more RNase inhibitor is used to treat particles isolated from 1 µl or more bodily fluid. Preferably, the RNase inhibitor is a protease, in which case, 1 AU is the protease activity that releases folin-positive amino acids and peptides corresponding to 1 µmol tyrosine per minute.

One surprising manifestation of the high quality nucleic acid extraction using the new method of the present invention is the ability to detect in an extraction of nucleic acids from particles such as microvesicles the existence of significant quantities of ribosomal RNA (rRNA). No prior studies are known to have demonstrated the detection of 18S and 28S rRNAs in nucleic acid extractions from particles. On the contrary, prior studies suggested that no or little rRNA is present in nucleic acid extracts from microvesicles (Skog et al., 2008; Taylor and Gercel-Taylor, 2008; Valadi et al., 2007). See also, the product description of ExoMir™ kit (Bioo Scientific Corp., Austin, Tex.).

In one embodiment, the extracted nucleic acid comprises RNA. In this instance, the RNA is preferably reverse-transcribed into complementary DNA (cDNA) before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching. Another example of the method comprises two separate steps: a first of reverse transcription to convert RNA into cDNA and a second step of quantifying the amount of cDNA using quantitative PCR. As demonstrated in the examples that follow, the RNAs extracted from nucleic acid-containing particles using the methods disclosed herein include many species of transcripts including, but not limited to, the transcripts that correspond to those for GAPDH, BRAF, KLK3, EGFR, and ribosomal 18S rRNA.

Nucleic acid amplification methods include, without limitation, polymerase chain reaction (PCR) (U.S. Pat. No. 5,219,727) and its variants such as in situ polymerase chain reaction (U.S. Pat. No. 5,538,871), quantitative polymerase chain reaction (U.S. Pat. No. 5,219,727), nested polymerase chain reaction (U.S. Pat. No. 5,556,773), self-sustained sequence replication and its variants (Guatelli et al., 1990), transcriptional amplification system and its variants (Kwoh et al., 1989), Qb Replicase and its variants (Miele et al., 1983), cold-PCR (Li et al., 2008), BEAMing (Li et al., 2006) or any other nucleic acid amplification methods, followed by the detection of the amplified molecules using techniques well known to those of skill in the art. Especially useful are those detection schemes designed for the detection of nucleic acid molecules if such molecules are present in very low numbers. The foregoing references are incorporated herein for their teachings of these methods. In other embodiment, the step of nucleic acid amplification is not performed. Instead, the extract nucleic acids are analyzed directly, e.g., through next-generation sequencing.

The analysis of nucleic acids present in the isolated particles is quantitative and/or qualitative. For quantitative analysis, the amounts (expression levels), either relative or absolute, of specific nucleic acids of interest within the isolated particles are measured with methods known in the art (described below). For qualitative analysis, the species of specific nucleic acids of interest within the isolated particles, whether wild type or variants, are identified with methods known in the art.

The present invention also includes various uses of the new methods of nucleic acid extraction from a biological sample for (i) aiding in the diagnosis of a subject, (ii) monitoring the progress or reoccurrence of a disease or other medical condition in a subject, or (iii) aiding in the evaluation of treatment efficacy for a subject undergoing or contemplating treatment for a disease or other medical condition; wherein the presence or absence of one or more biomarkers in the nucleic acid extraction obtained from the method is determined, and the one or more biomarkers are associated with the diagnosis, progress or reoccurrence, or treatment efficacy, respectively, of a disease or other medical condition.

The one or more biomarkers can be one or a collection of genetic aberrations, which is used herein to refer to the nucleic acid amounts as well as nucleic acid variants within the nucleic acid-containing particles. Specifically, genetic aberrations include, without limitation, over-expression of a gene (e.g., an oncogene) or a panel of genes, under-expression of a gene (e.g., a tumor suppressor gene such as p53 or RB) or a panel of genes, alternative production of splice variants of a gene or a panel of genes, gene copy number variants (CNV) (e.g., DNA double minutes) (Hahn, 1993), nucleic acid modifications (e.g., methylation, acetylation and phosphorylations), single nucleotide polymorphisms (SNPs), chromosomal rearrangements (e.g., inversions, deletions and duplications), and mutations (insertions, deletions, duplications, missense, nonsense, synonymous or any other nucleotide changes) of a gene or a panel of genes, which mutations, in many cases, ultimately affect the activity and function of the gene products, lead to alternative transcriptional splice variants and/or changes of gene expression level, or combinations of any of the foregoing.

The determination of such genetic aberrations can be performed by a variety of techniques known to the skilled practitioner. For example, expression levels of nucleic acids, alternative splicing variants, chromosome rearrangement and gene copy numbers can be determined by microarray analysis (see, e.g., U.S. Pat. Nos. 6,913,879, 7,364,848, 7,378,245, 6,893,837 and 6,004,755) and quantitative PCR. Particularly, copy number changes may be detected with the Illumina Infinium II whole genome genotyping assay or Agilent Human Genome CGH Microarray (Steemers et al., 2006). Nucleic acid modifications can be assayed by methods described in, e.g., U.S. Pat. No. 7,186,512 and patent publication WO/2003/023065. Particularly, methylation profiles may be determined by Illumina DNA Methylation OMA003 Cancer Panel. SNPs and mutations can be detected by hybridization with allele-specific probes, enzymatic mutation detection, chemical cleavage of mismatched heteroduplex (Cotton et al., 1988), ribonuclease cleavage of mismatched bases (Myers et al., 1985), mass spectrometry (U.S. Pat. Nos. 6,994,960, 7,074,563, and 7,198,893), nucleic acid sequencing, single strand conformation polymorphism (SSCP) (Orita et al., 1989), denaturing gradient gel electrophoresis (DGGE)(Fischer and Lerman, 1979a; Fischer and Lerman, 1979b), temperature gradient gel electrophoresis (TGGE) (Fischer and Lerman, 1979a; Fischer and Lerman, 1979b), restriction fragment length polymorphisms (RFLP) (Kan and Dozy, 1978a; Kan and Dozy, 1978b), oligonucleotide ligation assay (OLA), allele-specific PCR (ASPCR) (U.S. Pat. No. 5,639,611), ligation chain reaction (LCR) and its variants (Abravaya ct al., 1995; Landegren et al., 1988; Nakazawa et al., 1994), flow-cytometric heteroduplex analysis (WO/2006/113590) and combinations/modifications thereof. Notably, gone expression levels may be determined by the serial analysis of gene expression (SAGE) technique (Velculescu et al., 1995). In general, the methods for analyzing genetic aberrations are reported in numerous publications, not limited to those cited herein, and are available to skilled practitioners. The appropriate method of analysis will depend upon the specific goals of the analysis, the condition/history of the patient, and the specific cancer(s), diseases or other medical conditions to be detected, monitored or treated. The forgoing references are incorporated herein for their teaching of these methods.

Many biomarkers may be associated with the presence or absence of a disease or other medical condition in a subject. Therefore, detection of the presence or absence of such biomarkers in a nucleic acid extraction from isolated particles, according to the methods disclosed herein, may aid diagnosis of the disease or other medical condition in the subject. For example, as described in WO 2009/100029, detection of the presence or absence of the EGFRvIII mutation in nucleic acids extracted from microvesicles isolated from a patient serum sample may aid in the diagnosis and/or monitoring of glioblastoma in the patient. This is so because the expression of the EGFRvIII mutation is specific to some tumors and defines a clinically distinct subtype of glioma (Pelloski et al., 2007). For another example, as described in WO 2009/100029, detection of the presence or absence of the TMPRSS2-ERG fusion gene and/or PCA-3 in nucleic acids extracted from microvesicles isolated from a patient urine sample may aid in the diagnosis of prostate cancer in the patient.

Further, many biomarkers may help disease or medical status monitoring in a subject. Therefore, the detection of the presence or absence of such biomarkers in a nucleic acid extraction from isolated particles, according to the methods disclosed herein, may aid in monitoring the progress or reoccurrence of a disease or other medical condition in a subject. For example, as described in WO 2009/100029, the determination of matrix metalloproteinase (MMP) levels in nucleic acids extracted from microvesicles isolated from an organ transplantation patient may help to monitor the post-transplantation condition, as a significant increase in the expression level of MMP-2 after kidney transplantation may indicate the onset and/or deterioration of post-transplantation complications. Similarly, a significantly elevated level of MMP-9 after lung transplantation, suggests the onset and/or deterioration of bronchiolitis obliterans syndrome.

Many biomarkers have also been found to influence the effectiveness of treatment in a particular patient. Therefore, the detection of the presence or absence of such biomarkers in a nucleic acid extraction from isolated particles, according to the methods disclosed herein, may aid in evaluating the efficacy of a given treatment in a given patient. For example, as disclosed in Table 1 in the publication by Furnari et. al. (Furnari et al., 2007), biomarkers, e.g., mutations in a variety of genes, affect the effectiveness of specific medicines used in chemotherapy for treating brain tumors. The identification of these biomarkers in nucleic acids extracted from isolated particles from a biological sample from a patient may guide the selection of treatment for the patient.

One aspect of the present invention is further directed to a kit for use in the new methods disclosed herein. The kit is comprised of the following components: RNase inhibitor in quantity sufficient to mitigate adverse factors that prevent or might prevent high quality nucleic acid extraction; RNA purification reagent; optionally, lysis buffer; optionally, DNase; and optionally, instructions for using the foregoing reagents in the extraction of nucleic acids from isolated particles. The RNA purification reagent helps to purify the released nucleic acids. The lysis buffer helps to break open microvesicles so that their nucleic acid contents are released. The use of DNase may help enhance the quality of the extracted nucleic acids. The inclusion of DNase is optional because DNase digestion may sometimes be carried out on a nucleic acid purification column, as described in the second example under the section "Particle isolation and nucleic acid extraction from serum samples." The kit may also comprise instructions that detail the steps as appropriate for using the kit components in connection with the extraction of nucleic acids from isolated particles.

It should be understood that this invention is not limited to the particular methodologies, protocols and reagents, described herein, which may vary. The terminology used herein is for the purpose of describing particular embodiments only, and is not intended to limit the scope of the present invention, which is defined solely by the claims.

Examples of the disclosed subject matter are set forth below. Other features, objects, and advantages of the disclosed subject matter will be apparent from the detailed description, figures, examples and claims. Methods and materials substantially similar or equivalent to those described herein can be used in the practice or testing of the presently disclosed subject matter. Exemplary methods and materials are now described as follows.

Example 1

We obtained a 1 ml frozen serum sample from a normal, healthy human volunteer. The serum sample was filtered through a 0.8 µm filter (Millipore) and the filtrate was then stored at −80° C. for 24 hours. When the sample was thawed, 8 µl SuperaseIn was added. The sample was then centrifuged at 20,000 g (Hettich microcentrifuge) for 0.5 hour at 4° C. in an angle head rotor. The supernatant was removed and discarded. The pellet was re-suspended in 1.5 ml PBS and re-centrifuged at 20,000 g for another 0.5 hour. The supernatant was then removed and discarded. The pellet was treated with 8 µl SuperascIn (20 units/µl) for 1 minute and then re-suspended in RLT buffer plus 10 µl/ml betamercaptoethanol and processed using the Qiagen RNeasy Plus kit which features a DNA removal column. The nucleic acids were eluted in 16 µl nuclease-free $H_2O$.

We examined the quality of the extracted nucleic acids using an RNA Pico Chip on an Agilent Bioanalyzer. As shown in FIG. 1A, we detected the presence of the 18S and 28S rRNA in the extraction. The RNA Integrity Number (RIN), as calculated by the Bioanalyzer's software, was 8.5. In addition, in the extracted nucleic acids, we detected the presence of RNAs corresponding to the GAPDH, BRAF, and 18S RNA genes. We used 12 µl of the extracted RNA and reverse transcribed the RNA into cDNA using a Sensiscript kit (Qiagen). We then used 2 µl of the resulting cDNA product as templates to perform Real-time PCR. The primers used for the RT-PCR are commercially available from Applied Biosystems, as follows: Human GAPDH (part number 4326317E); BRAF (part number Hs00269944_m1); 18S rRNA (part number Hs99999901_s1). Each sample was run in triplicate on the PCR plate. The Ct values from the RT-PCR investigation are presented as average±SD. The Ct values for GAPDH, BRAF and 18S rRNA are 30.84±0.08, 36.76±0.22, and 15.09±0.21, respectively.

Therefore, using the new method, we were able to isolate nucleic acid-containing particles from serum samples. The nucleic acids extracted from the pelleted particles contained 18S and 28S rRNA. The quality of the nucleic acids produced a RIN of 8.5. Further, the extracted nucleic acids contain RNAs corresponding to at least GAPDH, BRAF and 18S rRNA genes, suggesting that the extracted nucleic acids from serum particles may include RNAs corresponding to many other genes.

Example 2

We obtained a 1 ml frozen serum sample from the same normal, healthy human volunteer as in Example 1 and filtered the serum through a 0.8 µm filter (Millipore) and the filtrate was then stored at −80° C. for 24 hours. The frozen sample was thawed on ice, and transferred into a 1.5 ml Eppendorf tube containing 8 µl SuperaseIn (Ambion Inc.). After the 20,000 g, 0.5 hour centrifugation step, the supernatant was set aside for further extraction as detailed in Example 3 below. The pellet was used for nucleic acid extraction employing a modified miRNeasy RNA extraction protocol. This modified protocol was more efficient at capturing the small RNAs (e.g., less than 200 nucleotides) than the manufacturer's protocol contained in the RNeasy Plus kit used in Example 1.

In this modified protocol, we used a mixture of DNAse/SuperaseIn to treat the pellet (TURBO DNA-Free™ kit, Ambion). The DNase could be optionally replaced by an on-column DNase step following the miRNeasy protocol. This treatment removed most DNA, including DNA potentially coming from inside the isolated particles. These DNA may affect RNA integrity when the extracted RNA quantity is very small. If on-column DNase treatment is selected, the pellet is treated with 8 µL SuperaseIn in 42 µL PBS. The mixture of DNase and SuperaseIn RNase inhibitor in this particular sample was made according to the following scheme. DNase 1 and DNase buffer is from TURBO DNA-Free™ kit from Ambion. SuperaseIn was at a concentration of 20 units/µL.
Per Sample:

| | |
|---|---|
| DNase 1 | 2 µL |
| DNase buffer (10X) | 5 µL |
| SuperaseIn | 8 µL |
| 1xPBS | 35 µL |
| | 50 µL |

The pellet was mixed with 50 µL of the DNase/SuperaseIn mixture as mentioned above and incubated at room temperature for 20 min in the centrifuge tube. Then 700 µl Qiazol lysis buffer (Qiagen) was added to each sample in the centrifuge tube and mixed by pipetting up and down 15 times to dissolve/re-suspend the pellet. The suspended pellet mixture was immediately transferred to an Eppendorf tube. Further nucleic acid extraction was then performed in a PCR hood. The tube with the pellet mixture was vortexed briefly and incubated at room temperature for 2-4 minutes before 140 µl chloroform was added into the tube containing the mixture. The tube was then capped, shaken vigorously for 20 seconds, incubated at room temperature for 2-3 minutes, and centrifuged for 15 minutes at 12,000 g at 4° C. The upper aqueous phase was transferred to a new collection tube into which, 1.5 volumes (usually 600 µl) of 100% ethanol was added and mixed thoroughly by pipetting up and down several times.

Up to 700 µl of the ethanol mixture, including any precipitate that may have formed, was transferred into an RNeasy Micro spin column (MinElute column stored @+4° C., the column comes with the RNeasy Micro kit) which was inserted in a 2 ml collection tube as supplied by the manufacturer, and centrifuged at 1000 g for 15 second at room temperature. The flow-through was discarded. The centrifugation step was repeated until all the remaining mixture had been added. Again, the flow-through was discarded. The nucleic acids on the column were then washed three times as follows: 1) 700 µL Buffer RWT was added onto the RNeasy MinElute spin column and centrifuged for 15 seconds at 8500 g to wash the column with the flow-through discarded; 2) 500 µL Buffer RPE was added onto the RNeasy MinElute spin column and centrifuged for 15 seconds at 8500 g to wash the column with the flow-through discarded; 3) repeat the Buffer RPE wash step except that the column was centrifuged for 2 minutes at 8500 g to dry the RNeasy Mini spin column membrane.

After the washing steps, the RNeasyMinElute spin column was inserted into a new 2 ml collection tube and centrifuged at 14000 g for 5 minutes to further dry the column membrane. The dried column was inserted into another new 1.5 ml collection tube and 16 µL RNase-free water was added onto the dried column membrane and incubated for 1 minute at room temperature. The nucleic acids were eluted by centrifugation for 1 minute at 8500 g. The volume of the eluted nucleic acids was about 14 µl.

Figure 1B:
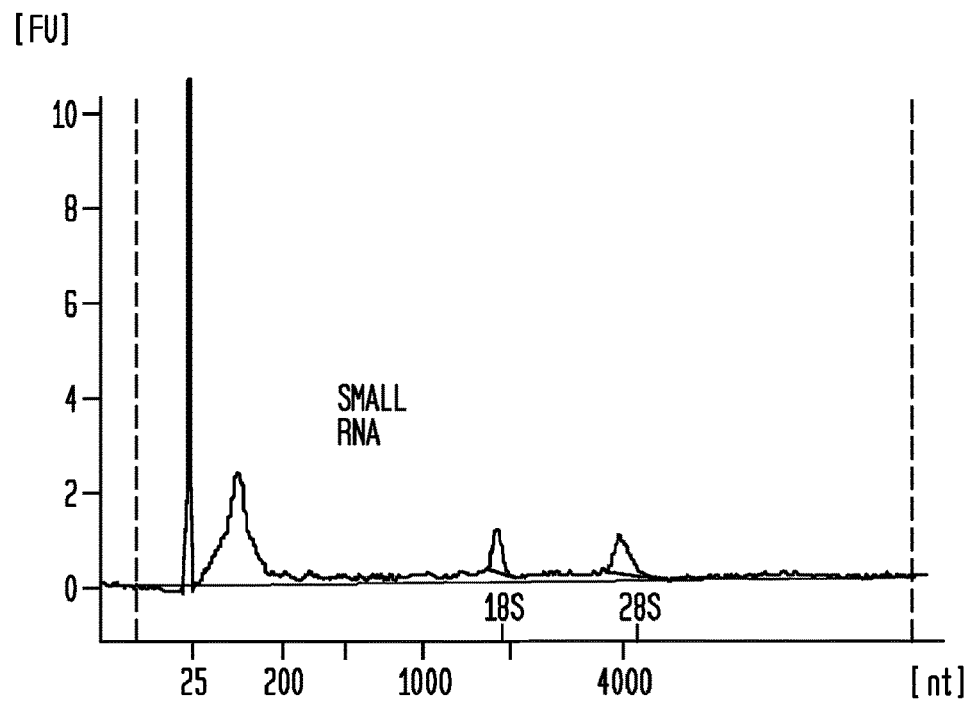

We analyzed the profile of the extracted nucleic acids. As shown in FIG. 1B, we detected peaks corresponding to 18S and 28S rRNAs, as well as peaks corresponding to small RNAs with sizes between 25 and 200 nucleotides. In addition, in the extracted nucleic acids, we detected the presence of RNAs corresponding to the GAPDH, BRAF, 18S RNA, and EGFR genes. We used 12 µl of the extracted RNA and reverse transcribed the RNA into cDNA using VILO™ kit (Invitrogen). The reverse transcription reaction mixture was made according to the following scheme (Table 1).

TABLE 1

Reverse transcription reaction mixture scheme.

| | (µl) × 1 reaction | ×4.4 |
|---|---|---|
| 5X VILO ™ Reaction Mix | 4 | 17.6 |
| 10X Superscript ® Enzyme Mix | 2 | 8.8 |
| RNA (up to 2.5 µg) | 12 | — |
| Nuclease free water | 2 | 8.8 |
| Total volume | 20 | |

The reverse transcription was performed in a verity PCR machine under the following conditions: 25° C. for 10 minutes, 42° C. for 70 minutes, 85° C. for 5 minutes, and was held in 4° C. before the reaction was stored at −20° C.

We then used 1 µl of the resulting cDNA product as templates to perform Real-time PCR. The primers used for the RT-PCR are commercially available from Applied Biosystems, as follows: Human GAPDH (part number 4326317E); BRAF (part number Hs00269944_m1); 18S rRNA (part number Hs99999901_s1); EGFR (part number HS01076088_m1). We repeated the real time-PCR experiments two times for each gene. The Ct values are shown in Table 2.

Therefore, using the new method as disclosed in this invention, we were able to isolate nucleic acid-containing particles from a serum sample. The nucleic acids extracted from the isolated particles contained 18S and 28S rRNA, as well as small RNAs. Further, the extracted nucleic acids contained RNAs for at least GAPDH, BRAF and 18S rRNA genes, suggesting that the extracted nucleic acids from serum particles may include RNAs corresponding to many other genes.

TABLE 2

The Ct values for the four genes
GAPDH, BRAF, 18S rRNA, and EGFR.

| Gene | Ct value |
|---|---|
| GAPDH | 31.12 |
|  | 31.07 |
| BRAF | 33.29 |
|  | 34.84 |
| 18S rRNA | 16.48 |
|  | 16.46 |
| EGFR | 37.05 |
|  | — |

Example 3

We started with the supernatant obtained in Example 2 after centrifuging the 1 ml serum sample at 20,000 g for 0.5 hour. The supernatant was further ultracentrifuged at 120,000 g for 80 minutes at 4-8° C. (Optima Max-XP Benchtop ultracentrifuge from Beckman). The deceleration was set at 7. Nucleic acids were then extracted from the pellet following the same protocol as detailed above in Example 2 starting from a treatment with DNase and SuperaseIn mixture. We analyzed the profile of the extracted nucleic acids, and performed reverse transcription and real time PCR analysis of the same four genes as in Example 2.

Figure 1C:
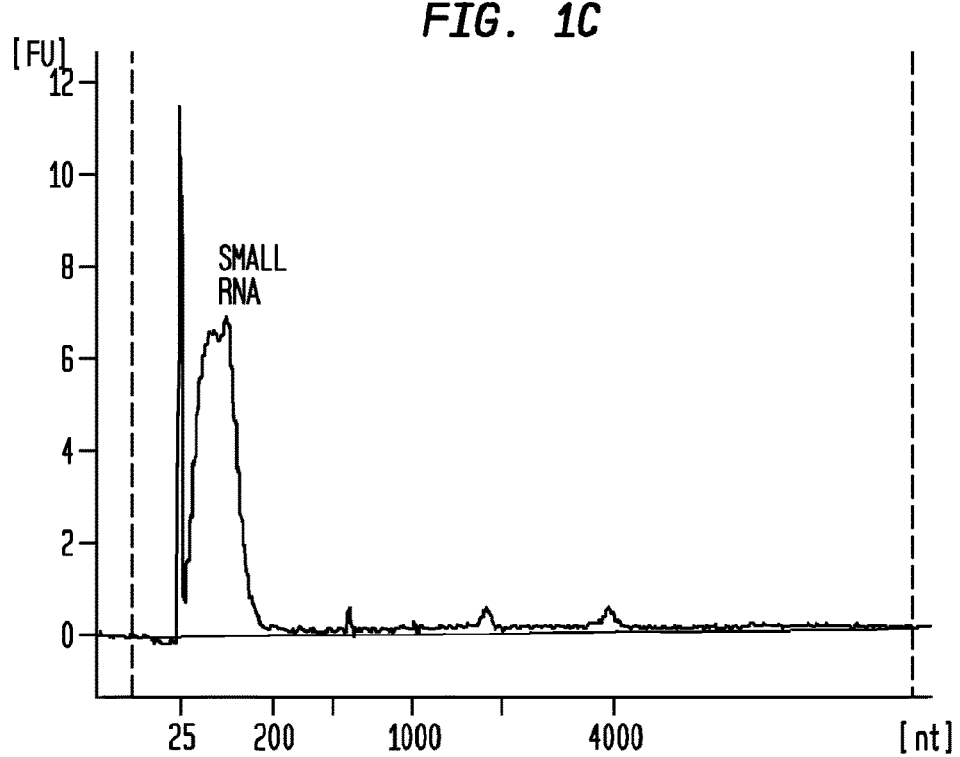

As shown in FIG. 1C, more small RNAs were seen in the extracted nucleic acids. The peaks between 25 and 200 nucleotides were higher than those in the FIG. 1B. Further the peaks shifted left in the interval between 25 and 200 nucleotides, suggesting the percentage of smaller RNAs was higher than the percentage seen in the extraction from Example 2.

As in Example 2, we also detected the RNAs corresponding to the four genes GAPDH, BRAF, 18S rRNA, and EGFR. The Ct values are shown in Table 3.

TABLE 3

The Ct values for the four genes
GAPDH, BRAF, 18S rRNA, and EGFR.

| Gene | Ct value |
|---|---|
| GAPDH | 34.71 |
|  | 34.97 |

TABLE 3-continued

The Ct values for the four genes
GAPDH, BRAF, 18S rRNA, and EGFR.

| Gene | Ct value |
|---|---|
| BRAF | — |
|  | 37.18 |
| 18S rRNA | 21.07 |
|  | 21.13 |
| EGFR | 32.8 |
|  | 31.83 |

Therefore, we were able to isolate nucleic acid-containing particles from the supernatant obtained in Example 2 after serum centrifugation at 20,000 g for 0.5 hour. The nucleic acids extracted from the particles pelleted from the supernatant contained more abundant small RNAs than the nucleic acids extracted from the particles initially pelleted in Example 2. Further, the extracted nucleic acids contained RNAs for at least GAPDH, BRAF and 18S rRNA genes, suggesting that the extracted nucleic acids from supernatant may include RNAs corresponding to many other genes.

Example 4

We started with a 24 ml serum sample from a healthy normal volunteer. The serum sample was filtered through a 0.8 m filter (Millipore) and the filtrate was then stored at −80° C. for 24 hours. The 24 ml serum sample was thawed and transferred into 24 tubes with 1 ml in each tube. Into each tube 8 µl SuperaseIn was then added and mixed with the serum sample.

We separated the 24 tubes into two groups each consisting of 12 tubes: group A and group B. For group A, the serum samples were centrifuged at 20,000 g for 0.5 hour and the pellet was used for nucleic acid extraction employing a modified miRNeasy RNA extraction protocol as described in Example 2. For group B, the serum samples were centrifuged at 120,000 g for 80 minutes and the pellet was used for nucleic acid extraction employing a modified miRNeasy RNA extraction protocol as described in Example 2.

Figure 3:
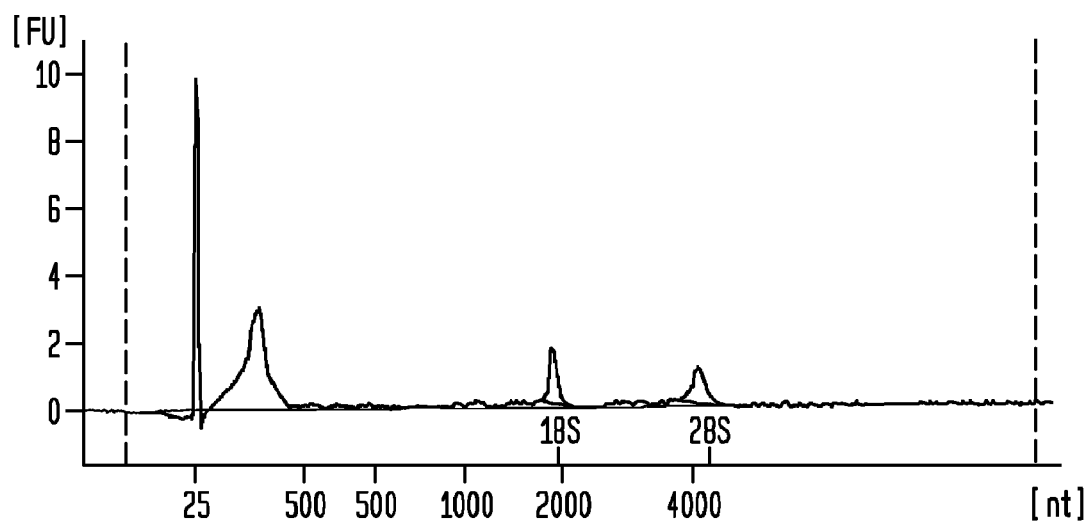
FIG. 3 is a Bioanalyzer plot depicting the analysis of nucleic acids extracted from particles isolated from serum samples in group A, Example 4 (20,000 g centrifugation speed).
Figure 4:
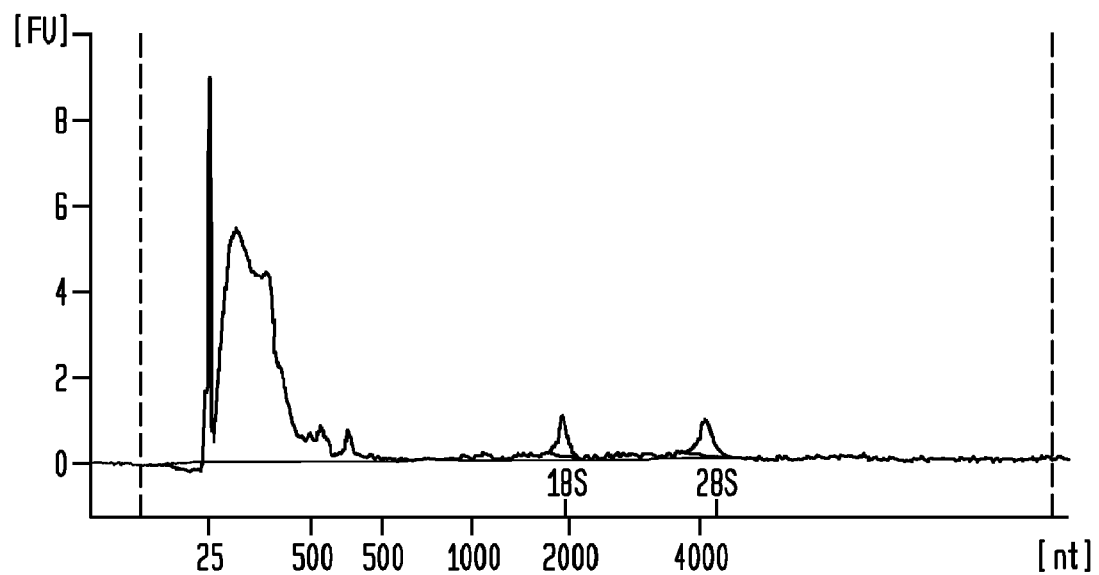
FIG. 4 is a Bioanalyzer plot depicting the analysis of nucleic acids extracted from particles isolated from serum samples in group B, Example 5 (120,000 g centrifugation speed).
Figure 5:
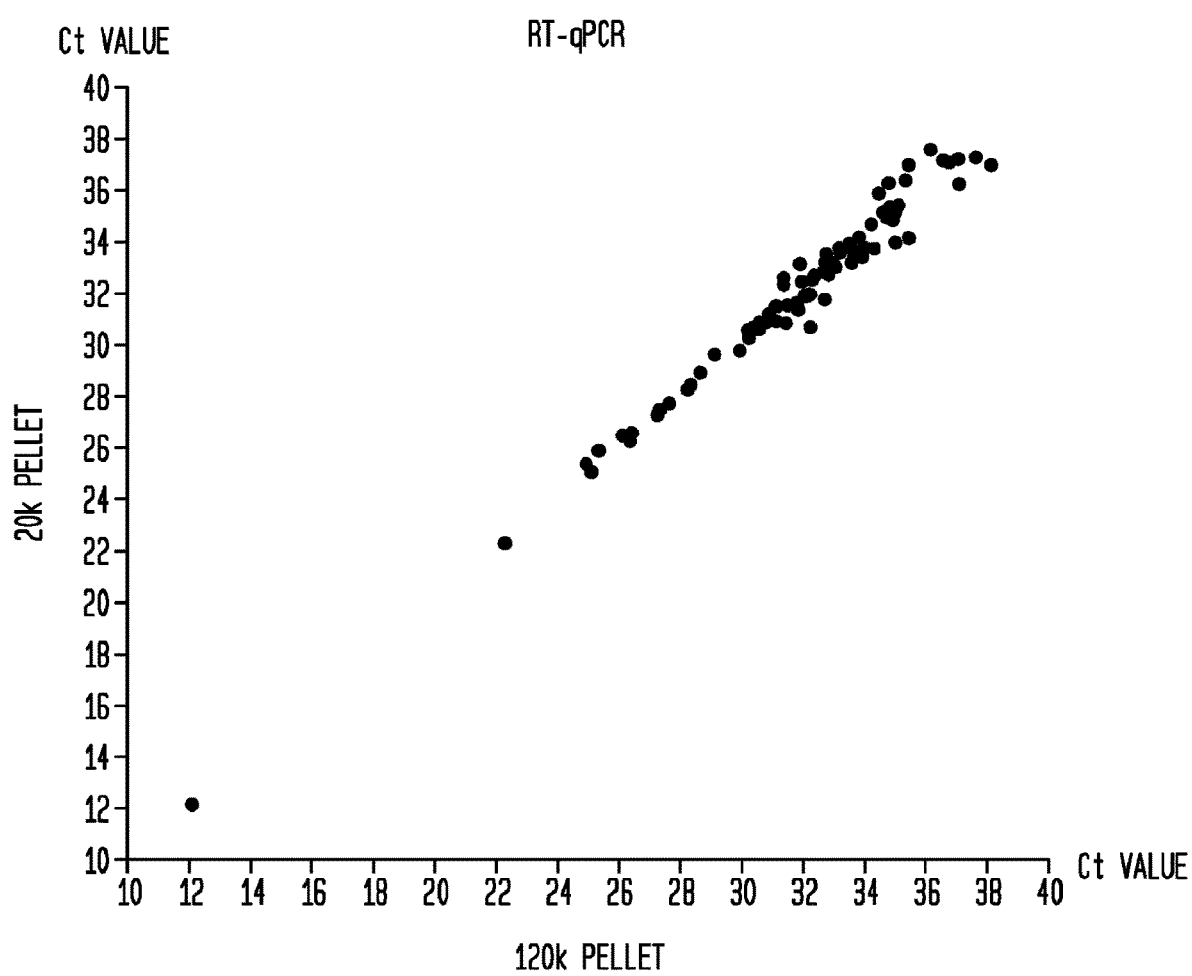
FIG. 5 is a plot depicting the comparison of Ct values for genes analyzed with the Taqman PCR array as between group A (Y-axis) and group B (X-axis) in Example 4.

We analyzed the profile of the extracted nucleic acids in both group A and group B. As shown in FIG. 3 (group A) and FIG. 4 (group B), we detected peaks corresponding to 18S and 28S rRNAs, as well as peaks corresponding to small RNAs with sizes between 25 and 300 nucleotides in both groups. The ratio of 28S rRNA over 18S rRNA was 0.9 and 1.2 for group A and group B, respectively.

We further detected the expression of many genes in the RNA extracted from both groups. The RNA extracted from particles pelleted from each of the serum samples was each reversed transcribed into cDNA using the VILO™ kit from Invitrogen as described in Example 2, and then analyzed using the TaqMan® array 96 Human Cell Surface Markers PCR plate from Applied Biosystems according to the manufacturer's protocol.

The Applied Biosystems assay IDs in the 96 Human Cell Surface Markers Taqman® PCR Array are shown in Table 4.

TABLE 4

Applied Biosystems assay IDs in the 96 Human Cell Surface Markers Taqman ® PCR Array

| ID | 1 | 2 | 3 | 4 | 5 | 6 |
|---|---|---|---|---|---|---|
| A | Hs99999901_s1 | Hs99999905_m1 | Hs99999909_m1 | Hs99999908_m1 | Hs99999903_m1 | Hs99999907_m1 |
| B | Hs00233455_m1 | Hs00704891_s1 | Hs00199894_m1 | Hs00174705_m1 | Hs99999192_m1 | Hs00233332_m1 |

TABLE 4-continued

Applied Biosystems assay IDs in the 96 Human Cell Surface Markers Taqman ® PCR Array

| | | | | | | |
|---|---|---|---|---|---|---|
| C | Hs00175568_m1 | Hs00609515_m1 | Hs00174796_m1 | Hs01099648_m1 | Hs01120071_m1 | Hs00174158_m1 |
| D | Hs00156390_m1 | Hs00934033_m1 | Hs00196191_m1 | Hs00174297_m1 | Hs00233564_m1 | Hs00269961_m1 |
| E | Hs00174762_m1 | Hs00175524_m1 | Hs01556595_m1 | Hs00164004_m1 | Hs01028971_m1 | Hs00153398_m1 |
| F | Hs01077044_m1 | Hs00417598_m1 | Hs01058806_g1 | Hs00219575_m1 | Hs00609563_m1 | Hs01106578_m1 |
| G | Hs00970273_g1 | Hs00233844_m1 | Hs01920599_gH | Hs00361185_m1 | Hs02339473_g1 | Hs00544819_m1 |
| H | Hs00169777_m1 | Hs00220767_m1 | Hs00374264_g1 | Hs00927900_m1 | Hs00949382_m1 | Hs00158980_m1 |

| ID | 7 | 8 | 9 | 10 | 11 | 12 |
|---|---|---|---|---|---|---|
| A | Hs99999902_m1 | Hs00609297_m1 | Hs99999910_m1 | Hs99999906_m1 | Hs00824723_m1 | Hs99999904_m1 |
| B | Hs00233509_m1 | Hs00939888_m1 | Hs00233515_m1 | Hs01588349_m1 | Hs00233533_m1 | Hs02379687_s1 |
| C | Hs00962186_m1 | Hs00181217_m1 | Hs99999100_s1 | Hs00163934_m1 | Hs00204397_m1 | Hs00198752_m1 |
| D | Hs00998119_m1 | Hs00236881_m1 | Hs00175478_m1 | Hs00188486_m1 | Hs01567025_m1 | Hs00233520_m1 |
| E | Hs00911250_m1 | Hs03044418_m1 | Hs00175210_m1 | Hs00923996_m1 | Hs00236330_m1 | Hs00758600_m1 |
| F | Hs01030384_m1 | Hs00907778_m1 | Hs00235006_m1 | Hs00158127_m1 | Hs01076873_m1 | Hs00174469_m1 |
| G | Hs00292551_m1 | Hs00159522_m1 | Hs00538076_m1 | Hs00941830_m1 | Hs00167166_m1 | Hs01573922_m1 |
| H | Hs00945155_m1 | Hs00533968_m1 | Hs00174277_m1 | Hs02576518_gH | Hs01003372_m1 | Hs00169795_m1 |

The gene symbols in the 96 Human Cell Surface Markers Taqman® PCR Array are shown in Table 5.

TABLE 5

Gene symbols corresponding to the 96 Human Cell Surface Markers Taqman ® PCR Array

| Symbol | 1 | 2 | 3 | 4 | 5 | 6 | 7 | 8 | 9 | 10 | 11 | 12 |
|---|---|---|---|---|---|---|---|---|---|---|---|---|
| A | 18S | GAPDH | HPRT1 | GUSB | ACTB | B2M | RPLP0 | HMBS | TBP | PGK1 | UBC | PPIA |
| B | ALCAM | C5AR1 | CD160 | CD163 | CD19 | CD1A | CD1C | CD1D | CD2 | CD209 | CD22 | CD24 |
| C | CD244 | CD247 | CD28 | CD37 | CD38 | CD3D | CD3G | CD4 | CD40 | CD40LG | CD5 | CD6 |
| D | CD63 | CD69 | CD7 | CD70 | CD72 | CD74 | CD79A | CD79B | CD80 | CD83 | CD86 | CD8A |
| E | CD8B | CD96 | CHST10 | COL1A1 | COL1A2 | CR2 | CSF1R | CTLA4 | DPP4 | ENG | FAS | FCER1A |
| F | FCER2 | FCGR1A; FCGR1B; FCGR1C | HLA-A; HLA-A29.1 | HLA-DRA | ICAM2 | IL1R2B1 | IL1R2 | IL2RA | ITGA1 | ITGA2 | ITGA3 | KLRB1 |
| G | KLRC1 | KLRD1 | KRT18 | KRT5 | KRT8, LOC728638 | MS4A1 | MYH10 | MYH9 | MYOCD | NCAM1 | NOS3 | NT5E |
| H | PECAM1 | RETN | S100A8 | SELP | ST6GAL1 | EPCAM | TEK | TNFRSF4 | TNFRSF8 | TPSAB1; TPSB2 | VCAM1 | VWF |

As shown in Table 6, we detected expression for most of the genes on the array. The expression levels are represented in Ct values.

TABLE 6

Gene expression levels in particles from each serum sample.

| Well | Target Gene Name | CT (Group A) | CT (Group B) |
|---|---|---|---|
| A1 | 18S-Hs99999901_s1 | 12.14 | 12.06 |
| A2 | GAPDH-Hs99999905_m1 | 26.47 | 26.18 |
| A3 | HPRT1-Hs99999909_m1 | 31.18 | 30.95 |
| A4 | GUSB-Hs99999908_m1 | 33.21 | 32.77 |
| A5 | ACTB-Hs99999903_m1 | 25.09 | 25.14 |
| A6 | B2M-Hs99999907_m1 | 22.32 | 22.30 |
| A7 | RPLP0-Hs99999902_m1 | 25.38 | 24.97 |
| A8 | HMBS-Hs00609297_m1 | 32.67 | 32.42 |
| A9 | TBP-Hs99999910_m1 | 33.51 | 32.85 |
| A10 | PGK1-Hs99999906_m1 | 28.39 | 28.38 |
| A11 | UBC-Hs00824723_m1 | 27.28 | 27.30 |
| A12 | PPIA-Hs99999904_m1 | 26.57 | 26.47 |
| B1 | ALCAM-Hs00233455_m1 | 35.85 | 34.58 |
| B2 | C5AR1-Hs00704891_s1 | 28.27 | 28.29 |
| B3 | CD160-Hs00199894_m1 | 34.93 | 34.82 |
| B4 | CD163-Hs00174705_m1 | 34.85 | 35.00 |
| B5 | CD19-Hs99999192_m1 | 33.76 | 33.24 |
| B6 | CD1A-Hs00233332_m1 | Undetermined | Undetermined |
| B7 | CD1C-Hs00233509_m1 | 35.13 | 34.70 |
| B8 | CD1D-Hs00939888_m1 | 33.79 | 34.10 |
| B9 | CD2-Hs00233515_m1 | 30.91 | 30.90 |
| B10 | CD209-Hs01588349_m1 | 37.52 | Undetermined |
| B11 | CD22-Hs00233533_m1 | 29.82 | 29.99 |
| B12 | CD24-Hs02379687_s1 | 30.55 | 30.25 |
| C1 | CD244-Hs00175568_m1 | 30.85 | 31.50 |
| C2 | CD247-Hs00609515_m1 | 30.64 | 30.44 |
| C3 | CD28-Hs00174796_m1 | 33.23 | 32.94 |
| C4 | CD37-Hs01099648_m1 | 30.59 | 30.41 |
| C5 | CD38-Hs01120071_m1 | 34.69 | 34.30 |
| C6 | CD3D-Hs00174158_m1 | 30.58 | 30.36 |
| C7 | CD3G-Hs00962186_m1 | 31.54 | 31.48 |
| C8 | CD4-Hs00181217_m1 | 33.24 | 33.65 |
| C9 | CD40-Hs99999100_s1 | 33.08 | 33.12 |
| C10 | CD40LG-Hs00163934_m1 | 33.71 | 33.64 |
| C11 | CD5-Hs00204397_m1 | 33.41 | 33.91 |
| C12 | CD6-Hs00198752_m1 | 33.47 | 33.99 |
| D1 | CD63-Hs00156390_m1 | 29.62 | 29.15 |
| D2 | CD69-Hs00934033_m1 | 32.52 | 32.32 |
| D3 | CD7-Hs00196191_m1 | 31.64 | 31.83 |
| D4 | CD70-Hs00174297_m1 | 36.99 | 38.20 |
| D5 | CD72-Hs00233564_m1 | 32.82 | 32.68 |
| D6 | CD74-Hs00269961_m1 | 28.93 | 28.71 |
| D7 | CD79A-Hs00998119_m1 | 31.48 | 31.20 |

TABLE 6-continued

Gene expression levels in particles from each serum sample.

| Well | Target Gene Name | CT (Group A) | CT (Group B) |
|---|---|---|---|
| D8 | CD79B-Hs00236881_m1 | 31.93 | 32.11 |
| D9 | CD80-Hs00175478_m1 | 37.80 | Undetermined |
| D10 | CD83-Hs00188486_m1 | 33.11 | 31.97 |
| D11 | CD86-Hs01567025_m1 | 35.40 | 35.20 |
| D12 | CD8A-Hs00233520_m1 | 31.38 | 31.89 |
| E1 | CD8B-Hs00174762_m1 | 33.93 | 33.52 |
| E2 | CD96-Hs00175524_m1 | 34.14 | 33.82 |
| E3 | CHST10-Hs01556595_m1 | 37.54 | Undetermined |
| E4 | COL1A1-Hs00164004_m1 | Undetermined | Undetermined |
| E5 | COL1A2-Hs01028971_m1 | 36.61 | Undetermined |
| E6 | CR2-Hs00153398_m1 | 35.31 | 34.87 |
| E7 | CSF1R-Hs00911250_m1 | 37.17 | 36.63 |
| E8 | CTLA4-Hs03044418_m1 | 36.24 | 37.17 |
| E9 | DPP4-Hs00175210_m1 | 33.75 | 34.37 |
| E10 | ENG-Hs00923996_m1 | 32.34 | 31.41 |
| E11 | FAS-Hs00236330_m1 | 33.77 | 33.55 |
| E12 | FCER1A-Hs00758600_m1 | 37.26 | 37.73 |
| F1 | FCER2-Hs01077044_m1 | 34.15 | 33.91 |
| F2 | FCGR1A; FCGR1B; FCGR1C-Hs00417598_m1 | 33.29 | 32.87 |
| F3 | HLA-A; HLA-A29.1-Hs01058806_g1 | 27.51 | 27.40 |
| F4 | HLA-DRA-Hs00219575_m1 | 27.75 | 27.69 |
| F5 | ICAM2-Hs00609563_m1 | 30.65 | 30.61 |
| F6 | IL12RB1-Hs01106578_m1 | 32.77 | 32.87 |
| F7 | IL1R2-Hs01030384_m1 | 32.45 | 31.97 |
| F8 | IL2RA-Hs00907778_m1 | 35.00 | 34.78 |
| F9 | ITGA1-Hs00235006_m1 | 31.78 | 32.76 |
| F10 | ITGA2-Hs00158127_m1 | 37.80 | Undetermined |
| F11 | ITGA3-Hs01076873_m1 | 37.20 | 37.14 |
| F12 | KLRB1-Hs00174469_m1 | 28.43 | 28.37 |
| G1 | KLRC1-Hs00970273_g1 | 34.15 | 35.50 |
| G2 | KLRD1-Hs00233844_m1 | 31.96 | 32.27 |
| G3 | KRT18-Hs01920599_gH | 32.59 | 31.41 |
| G4 | KRT5-Hs00361185_m1 | 37.99 | Undetermined |
| G5 | KRT8; LOC728638-Hs02339473_g1 | Undetermined | 38.60 |
| G6 | MS4A1-Hs00544819_m1 | 30.92 | 31.20 |
| G7 | MYH10-Hs00292551_m1 | 35.32 | 34.88 |
| G8 | MYH9-Hs00159522_m1 | 26.30 | 26.40 |
| G9 | MYOCD-Hs00538076_m1 | Undetermined | Undetermined |
| G10 | NCAM1-Hs00941830_m1 | 36.99 | 35.55 |
| G11 | NOS3-Hs00167166_m1 | 37.07 | 36.85 |
| G12 | NT5E-Hs01573922_m1 | 33.57 | 33.26 |
| H1 | PECAM1-Hs00169777_m1 | 30.28 | 30.28 |
| H2 | RETN-Hs00220767_m1 | 35.14 | 35.08 |
| H3 | S100A8-Hs00374264_g1 | 25.88 | 25.40 |
| H4 | SELP-Hs00927900_m1 | 30.85 | 30.65 |
| H5 | ST6GAL1-Hs00949382_m1 | 31.55 | 31.57 |
| H6 | EPCAM-Hs00158980_m1 | 37.58 | 36.23 |
| H7 | TEK-Hs00945155_m1 | 30.68 | 32.30 |
| H8 | TNFRSF4-Hs00533968_m1 | 33.96 | 35.10 |
| H9 | TNFRSF8-Hs00174277_m1 | 35.19 | 34.99 |
| H10 | TPSAB1; TPSB2-Hs02576518_gH | Undetermined | Undetermined |
| H11 | VCAM1-Hs01003372_m1 | 36.27 | 34.87 |
| H12 | VWF-Hs00169795_m1 | 36.39 | 35.45 |

We compared the Ct values between the two groups for each of the genes tested and found that the mRNA content in the two groups was very similar. Therefore, we were able to isolate nucleic acid-containing particles from the serum sample by centrifugation at either 20,000 g for 0.5 hour or 120,000 g for 80 minutes. The nucleic acids extracted from the isolated particles contained both 18S and 28S rRNA. In addition, the mRNA content obtained with a 20,000 g centrifugation speed was similar to the mRNA content obtained with a 120,000 g centrifugation speed. Further, the extracted nucleic acids from each of the pellets contained mRNAs corresponding to most of the genes tested using the Taqman array.

Example 5: Particle Isolation and Nucleic Acid Extraction from Urine Samples

We started with a 10 ml spot urine sample from normal, healthy human volunteers. The sample had been stored at 4° C. for a week. The urine sample was filtered through 0.8 μm filters (Nalgene). The filtrate was then centrifuged at 20,000 g for 1 hour at 4° C. in an angle head rotor. The supernatant was removed and discarded. The pellets were lysed in RLT buffer plus 10 μl/ml betamercaptoethanol and processed using the Qiagen RNeasy Plus kit. The nucleic acids were eluted in 16 μl nuclease-free $H_2O$.

Figure 2:
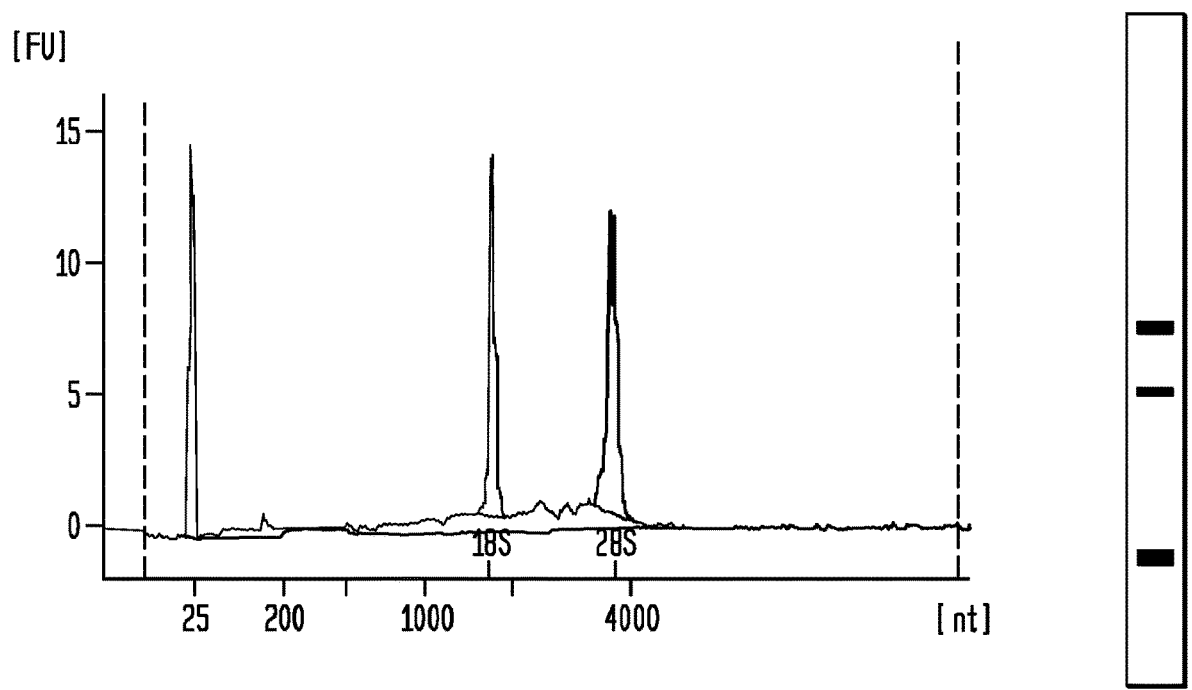
FIG. 2 is a Bioanalyzer plot depicting the analysis of nucleic acids extracted from particles isolated from a urine sample, as described in Example 5 below, and a pseudogel depicting the content of the same nucleic acid extraction. The plot and the pseudogel were generated by an Agilent Bioanalyzer.

We examined the quality of the extracted nucleic acids using an Agilent Bioanalyzer. As shown in FIG. 2, we detected the presence of the 18S and 28S rRNA in the extractions. The RNA Integrity Number (RIN), as calculated by the Bioanalyzer's software, was 9.1. In addition, in the extracted nucleic acids, we detected the presence of RNAs corresponding to the GAPDH, KLK3, and 18S RNA genes. We reverse transcribed 12 μl of the extracted RNA into cDNA using a Sensiscript kit (Qiagen). We then used 2 μl of the resulting cDNA product as templates to perform Real-time PCR. The primers used for the RT-PCR are commercially available from Applied Biosystems, as follows: Human GAPDH (part number 4326317E); KLK3 (part number Hs03063374_m1); 18S rRNA (part number Hs99999901_s1). Each sample was run in triplicate on the PCR plate. The Ct values from the RT-PCR investigation are presented as average±SD. The Ct values for GAPDH, KLK3 and 18S rRNA are 26.96±0.02, 30.18±0.01, and 12.22±0.15, respectively.

Therefore, using the new method as disclosed in this invention, we were able to isolate nucleic acid-containing particles from urine samples. The nucleic acids extracted from the pelleted particles contained 18S and 28S rRNA. The quality of the nucleic acids produced a RIN of 9.1. Further, the extracted nucleic acids contain RNAs for at least GAPDH, KLK3 and 18S rRNA genes, suggesting that the extracted nucleic acids from urine particles may include RNAs corresponding to many other genes.

While the present invention has been disclosed with reference to certain embodiments, numerous modifications, alterations, and changes to the described embodiments are possible without departing from the full scope of the invention, as described in the appended specification and claims.

REFERENCES

Abravaya, K., J. J. Carrino, S. Muldoon, and H. H. Lee. 1995. Detection of point mutations with a modified ligase chain reaction (Gap-LCR). *Nucleic Acids Res.* 23:675-82.

Chen, C., J. Skog, C. H. Hsu, R. T. Lessard, L. Balaj, T. Wurdinger, B. S. Carter, X. O. Breakefield, M. Toner, and D. Irimia. 2010. Microfluidic isolation and transcriptome analysis of serum microvesicles. *Lab Chip.* 10:505-11.

Cheruvanky, A., H. Zhou, T. Pisitkun, J. B. Kopp, M. A. Knepper, P. S. Yuen, and R. A. Star. 2007. Rapid isolation of urinary exosomal biomarkers using a nanomembrane ultrafiltration concentrator. *Am J Physiol Renal Physiol.* 292:F1657-61.

Cocucci, E., G. Racchetti, and J. Meldolesi. 2009. Shedding microvesicles: artefacts no more. *Trends Cell Biol.* 19:43-51.

Cotton, R. G., N. R. Rodrigues, and R. D. Campbell. 1988. Reactivity of cytosine and thymine in single-base-pair mismatches with hydroxylamine and osmium tetroxide and its application to the study of mutations. *Proc Natl Acad Sci USA.* 85:4397-401.

Fischer, S. G., and L. S. Lerman. 1979a. Length-independent separation of DNA restriction fragments in two-dimensional gel electrophoresis. *Cell.* 16:191-200.

Fischer, S. G., and L. S. Lerman. 1979b. Two-dimensional electrophoretic separation of restriction enzyme fragments of DNA. *Methods Enzymol.* 68:183-91.

Furnari, F. B., T. Fenton, R. M. Bachoo, A. Mukasa, J. M. Stommel, A. Stegh, W. C. Hahn, K. L. Ligon, D. N. Louis, C. Brennan, L. Chin, R. A. DePinho, and W. K. Cavenee. 2007. Malignant astrocytic glioma: genetics, biology, and paths to treatment. *Genes Dev.* 21:2683-710.

Guatelli, J. C., K. M. Whitfield, D. Y. Kwoh, K. J. Barringer, D. D. Richman, and T. R. Gingeras. 1990. Isothermal, in vitro amplification of nucleic acids by a multienzyme reaction modeled after retroviral replication. *Proc Natl Acad Sci USA.* 87:1874-8.

Hahn, P. J. 1993. Molecular biology of double-minute chromosomes. *Bioessays.* 15:477-84.

Kan, Y. W., and A. M. Dozy. 1978a. Antenatal diagnosis of sickle-cell anaemia by D.N.A. analysis of amniotic-fluid cells. *Lancet.* 2:910-2.

Kan, Y. W., and A. M. Dozy. 1978b. Polymorphism of DNA sequence adjacent to human beta-globin structural gene: relationship to sickle mutation. *Proc Natl Acad Sci USA.* 75:5631-5.

Kwoh, D. Y., G. R. Davis, K. M. Whitfield, H. L. Chappelle, L. J. DiMichele, and T. R. Gingeras. 1989. Transcription-based amplification system and detection of amplified human immunodeficiency virus type 1 with a bead-based sandwich hybridization format. *Proc Natl Acad Sci USA.* 86:1173-7.

Landegren, U., R. Kaiser, J. Sanders, and L. Hood. 1988. A ligase-mediated gene detection technique. *Science.* 241:1077-80.

Li, J., L. Wang, H. Mamon, M. H. Kulke, R. Berbeco, and G. M. Makrigiorgos. 2008. Replacing PCR with COLD-PCR enriches variant DNA sequences and redefines the sensitivity of genetic testing. *Nat Med.* 14:579-84.

Li, M., F. Diehl, D. Dressman, B. Vogelstein, and K. W. Kinzler. 2006. BEAMing up for detection and quantification of rare sequence variants. *Nat Methods.* 3:95-7.

Miele, E. A., D. R. Mills, and F. R. Kramer. 1983. Autocatalytic replication of a recombinant RNA. *J Mol Biol.* 171:281-95.

Miranda, K. C., D. T. Bond, M. McKee, J. Skog, T. G. Paunescu, N. Da Silva, D. Brown, and L. M. Russo. 2010. Nucleic acids within urinary exosomes/microvesicles are potential biomarkers for renal disease. *Kidney Int.* 78:191-9.

Myers, R. M., Z. Larin, and T. Maniatis. 1985. Detection of single base substitutions by ribonuclease cleavage at mismatches in RNA:DNA duplexes. *Science.* 230:1242-6.

Nakazawa, H., D. English, P. L. Randell, K. Nakazawa, N. Martel, B. K. Armstrong, and H. Yamasaki. 1994. UV and skin cancer: specific p53 gene mutation in normal skin as a biologically relevant exposure measurement. *Proc Natl Acad Sci USA.* 91:360-4.

Nilsson, J., J. Skog, A. Nordstrand, V. Baranov, L. Mincheva-Nilsson, X. O. Breakefield, and A. Widmark. 2009. Prostate cancer-derived urine exosomes: a novel approach to biomarkers for prostate cancer. *Br J Cancer.* 100:1603-7.

Orita, M., H. Iwahana, H. Kanazawa, K. Hayashi, and T. Sekiya. 1989. Detection of polymorphisms of human DNA by gel electrophoresis as single-strand conformation polymorphisms. *Proc Natl Acad Sci USA.* 86:2766-70.

Orozco, A. F., and D. E. Lewis. 2010. Flow cytometric analysis of circulating microparticles in plasma. *Cytometry A.* 77:502-14.

Pelloski, C. E., K. V. Ballman, A. F. Furth, L. Zhang, E. Lin, E. P. Sulman, K. Bhat, J. M. McDonald, W. K. Yung, H. Colman, S. Y. Woo, A. B. Heimberger, D. Suki, M. D. Prados, S. M. Chang, F. G. Barker, 2nd, J. C. Buckner, C. D. James, and K. Aldape. 2007. Epidermal growth factor receptor variant III status defines clinically distinct subtypes of glioblastoma. *J Clin Oncol.* 25:2288-94.

Raposo, G., H. W. Nijman, W. Stoorvogel, R. Liejendekker, C. V. Harding, C. J. Melief, and H. J. Geuze. 1996. B lymphocytes secrete antigen-presenting vesicles. *J Exp Med.* 183:1161-72.

Skog, J., T. Wurdinger, S. van Rijn, D. H. Meijer, L. Gainche, M. Sena-Esteves, W. T. Curry, Jr., B. S. Carter, A. M. Krichevsky, and X. O. Breakefield. 2008. Glioblastoma microvesicles transport RNA and proteins that promote tumour growth and provide diagnostic biomarkers. *Nat Cell Biol.* 10:1470-6.

Steemers, F. J., W. Chang, G. Lee, D. L. Barker, R. Shen, and K. L. Gunderson. 2006. Whole-genome genotyping with the single-base extension assay. *Nat Methods.* 3:31-3.

Stoorvogel, W., M. J. Kleijmeer, H. J. Geuze, and G. Raposo. 2002. The biogenesis and functions of exosomes. *Traffic.* 3:321-30.

Taylor, D. D., and C. Gercel-Taylor. 2008. MicroRNA signatures of tumor-derived exosomes as diagnostic biomarkers of ovarian cancer. *Gynecol Oncol.* 110:13-21.

Thery, C., L. Zitvogel, and S. Amigorena. 2002. Exosomes: composition, biogenesis and function. *Nat Rev Immunol.* 2:569-79.

Valadi, H., K. Ekstrom, A. Bossios, M. Sjostrand, J. J. Lee, and J. O. Lotvall. 2007. Exosome-mediated transfer of mRNAs and microRNAs is a novel mechanism of genetic exchange between cells. *Nat Cell Biol.* 9:654-9.

Velculescu, V. E., L. Zhang, B. Vogelstein, and K. W. Kinzler. 1995. Serial analysis of gene expression. *Science.* 270:484-7.

The invention claimed is:

1. A method for extracting nucleic acids from a biological sample from a subject, comprising the steps of:
   a. isolating microvesicles comprising exosomes from the biological sample by one or more centrifugation procedures to pellet the microvesicles from the biological sample,
      wherein none of the centrifugation procedures are performed at a speed exceeding about 20,000 g, and
      wherein none of the centrifugation procedures use nanomembrane ultrafiltration concentration; and
   b. extracting nucleic acids from the isolated, pelleted microvesicles comprising exosomes,
      wherein 18S and 28S rRNAs are detectable in the extracted nucleic acids, and
      wherein the ratio of the amount of 18S rRNA to the amount of 28S rRNA, as detected in the extracted nucleic acids, is about 0.5 to about 1.0.

2. The method of claim 1, wherein the biological sample is a body fluid.

3. The method of claim 2, wherein the body fluid is a serum, urine, or spinal fluid sample from the subject.

4. The method of claim 3, wherein the subject is a human or other mammal.

5. The method of claim 1, wherein the extracted nucleic acids comprise RNA, DNA, or both RNA and DNA.

6. The method of claim 1, wherein the extracted nucleic acids comprise one or more nucleic acids having a sequence more than 90% homologous to the nucleic acid sequence corresponding to any of the genes consisting of EGFR, BRAF, KLK3, 18S, GAPDH, HPRT1, GUSB, ACTB, B2M, RPLP0, HMBS, TBP, PGK1, UBC, PPIA, ALCAM, C5AR1, CD160, CD163, CD19, CD1A, CD1C, CD1D, CD2, CD209, CD22, CD24, CD244, CD247, CD28, CD37, CD38, CD3D, CD3G, CD4, CD40, CD4OLG, CD5, CD6, CD63, CD69, CD7, CD70, CD72, CD74, CD79A, CD79B, CD80, CD83, CD86, CD8A, CD8B, CD96, CHST10, COL1A1, COL1A2, CR2, CSF1R, CTLA4, DPP4, ENG, FAS, FCER1A, FCER2, FCGR1A/FCGR1B/FCGR1C, HLA-A/HLA-A29.1, HLA-DRA, ICAM2, IL 12RB1, IL1R2, IL2RA, ITGA1, ITGA2, ITGA3, KLRB1, KLRC1, KLRD1, KRT18, KRT5, KRT8/LOC728638, MS4A1, MYH10, MYH9, MYOCD, NCAM1, NOS3, NT5E, PECAM1, RETN, S100A8, SELP, ST6GAL1, EPCAM, TEK, TNFRSF4, TNFRSF8, TPSAB1/TPSB2, VCAM1, or VWF.

7. The method of claim 1, wherein the ratio of the amount of 18S rRNA to the amount of 28S rRNA, as detected in the extracted nucleic acids, is about 0.5.

8. The method of claim 1, further comprising treating the biological sample and/or the isolated microvesicles with DNase, RNase inhibitor, or DNase and RNase inhibitor.

9. The method of claim 1, further comprising treating the biological sample with RNase inhibitor before isolating the microvesicles.

* * * * *